US008155403B2

(12) United States Patent
Tschirren et al.

(10) Patent No.: US 8,155,403 B2
(45) Date of Patent: Apr. 10, 2012

(54) METHODS AND DEVICES FOR AIRWAY TREE LABELING AND/OR MATCHING

(75) Inventors: Juerg Tschirren, Iowa City, IA (US); Milan Sonka, Iowa City, IA (US); Joseph Reinhardt, Iowa City, IA (US); Geoffrey McLennan, Iowa City, IA (US); Eric Hoffman, Iowa City, IA (US)

(73) Assignee: University of Iowa Research Foundation, Iowa City, IA (US)

( * ) Notice: Subject to any disclaimer, the term of this patent is extended or adjusted under 35 U.S.C. 154(b) by 2104 days.

(21) Appl. No.: 11/122,974

(22) Filed: May 5, 2005

(65) Prior Publication Data
US 2006/0030958 A1    Feb. 9, 2006

Related U.S. Application Data

(60) Provisional application No. 60/568,184, filed on May 5, 2004.

(51) Int. Cl.
*G06K 9/00*    (2006.01)
(52) U.S. Cl. ......... 382/128; 382/130; 382/131; 382/132
(58) Field of Classification Search ................... 382/259, 382/128, 130–132; 600/117, 407, 420; 607/88
See application file for complete search history.

(56) References Cited

U.S. PATENT DOCUMENTS
2002/0161296 A1*  10/2002  Kuth et al. .................... 600/420

OTHER PUBLICATIONS

"Preliminary Program of the ASCI 2004 Conference" Port Zelande, Jun. 2-4, 2004 (version May 14).
2 pages printed from www.isprs.org/istanbul2004 on Feb. 12, 2005.
27 pages printed from www.isprs.org/istanbul2004/comm5/comm5. html on Feb. 12, 2005.
Carraghan and Pardalos, "An exact algorithm for the maximum clique problem," Operations Research Letters, 9:375-382, 1990.
Gorte and Pfeifer, "3D image processing to reconstruct trees from laser scans," date unknown.
Gorte and Pfeifer, "Structuring laser-scanned trees using 3D mathematical morphology," date unknown.
Kitaoka et al., "Automated Nomenclature labeling of the bronchial tree in 3D-CT lung images," Lecture Notes in Computer Science, vol. 2489, pp. 1-11, 2002.
Kitaoka et al., "Automated Nomenclature Labeling of the Bronchial Tree in 3D-CT Lung Images," MICCAI2002, Tokyo, Japan, 1-11, 2002.
Mori et al., "Automated anatomical labeling of the bronchial branch and its application to the virtual bronchoscopy system," IEEE Transactions on Medical Imaging, 19:103-114, 2000.
Ostergard, "A fast algorithm for the maximum clique problem," Discrete Appl. Math. 120 195-205, 2002.

(Continued)

*Primary Examiner* — Claire X Wang
(74) *Attorney, Agent, or Firm* — Fulbright & Jaworski L.L.P.

(57) ABSTRACT

Devices, such as computer readable media, and methods, such as automated methods, for labeling and/or matching. Some of the devices and methods are particularly useful for anatomical labeling of human airway trees. Some of the devices and methods are particularly useful for matching branch-points of human airway trees from represented in two or more graphs.

38 Claims, 16 Drawing Sheets
(4 of 16 Drawing Sheet(s) Filed in Color)

OTHER PUBLICATIONS

Pal'agyi et al., "Quantitative analysis of intrathoracic airway trees: methods and validation," Proc. 18th Int. Conf. Information Processing in Medical Imaging, IPMI2003, Ambleside, UK, Lecture Notes in Computer Science 2732, Springer, pp. 222-233, 2003.

Park, "Registration of linear structures in 3-D medical images," Ph.D. dissertation, Osaka University, Japan, Department of Informatics and Mathematical Science, 2002.

Pelillo et al., "Matching Hierarchical Structures Using Association Graphs," IEEE Trans. Pattern Analysis and Machine Intelligence, vol. 21, No. 11, pp. 1105-1120, 1999.

Pisupati et al., "Geometric tree matching with applications to 3D lung structures," Proceedings of the Twelfth Annual Symposium on Computational Geometry, pp. 419-420, May 24-26, 1996.

Pisupati et al., "Tracking 3-D pulmonary tree structures," Proceedings of the Workshop on Mathematical Methods in Biomedical Image Analysis, 6 1996, pp. 160-169.

Tschirren et al., "Fully Automated Segmentation, Skeletonization, and Branchpoint Matching in Human Intrathoracic Airway Trees" Radiological Society of North America, RSNA, 88th Scientific Assembly and Annual Meeting, Chicago, IL, 2002.

Tschirren et al., "Airway tree segmentation using adaptive regions of interest," Medical Imaging 2004: Physiology, Function, and Structure from Medical Images, Proceedings of the SPIE, vol. 5369, pp. 117-124 (2004).

Tschirren et al., "Segmentation, Skeletonization, and Branchpoint Matching—A Fully Automated Quantitative Evaluation of Human Intrathoracic Airway Trees," Medical Image Computing and Computer-Assisted Intervention—MICCAI 2002: 5th International Conference, Tokyo, Japan, Sep. 25-28, 2002.

Tschirren et al., "Branchpoint labeling and matching in human airway trees," Medical Imaging 2003: Physiology and Function: Methods, Systems, and Applications, Proceedings of the SPIE, vol. 5031, pp. 187-194 (2003). Shipped to customers on May 5, 2003 and received by customers after May 5, 2003.

Tschirren, "Segmentation, anatomical labeling, branchpoint matching, and quantitative analysis of human airway trees in volumetric CT images," Ph.D. Thesis, University of Iowa, Aug. 2003.

Tschirren, "Segmentation, branchpoint matching and anatomical labeling of human airway trees in volumetric CT images," slides presented at Ph.D. defense, which occurred on Jul. 10, 2003.

* cited by examiner

FIG. 2

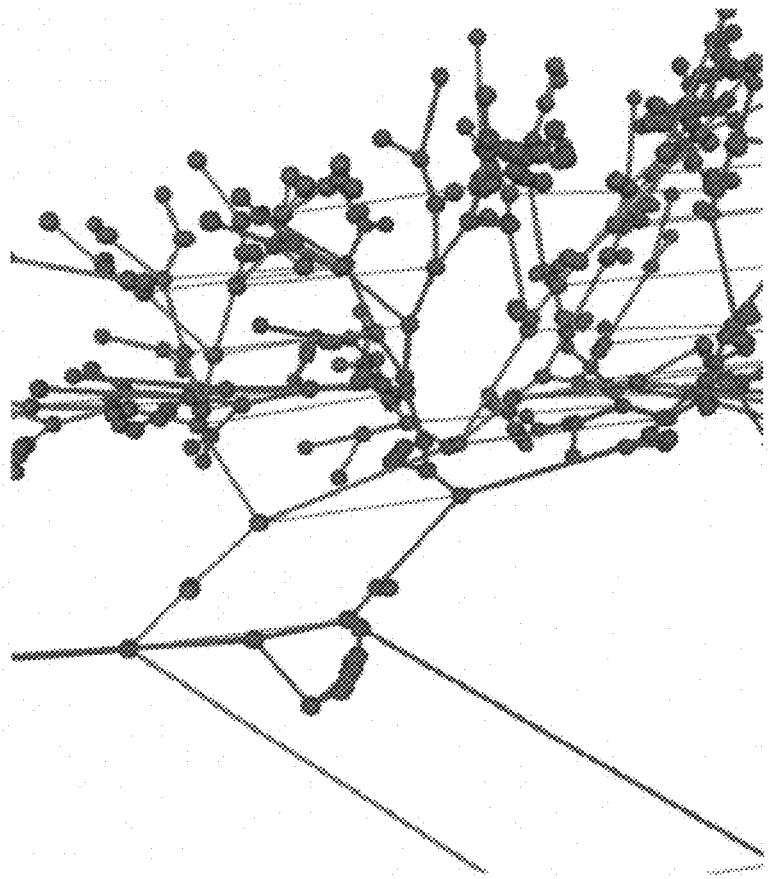
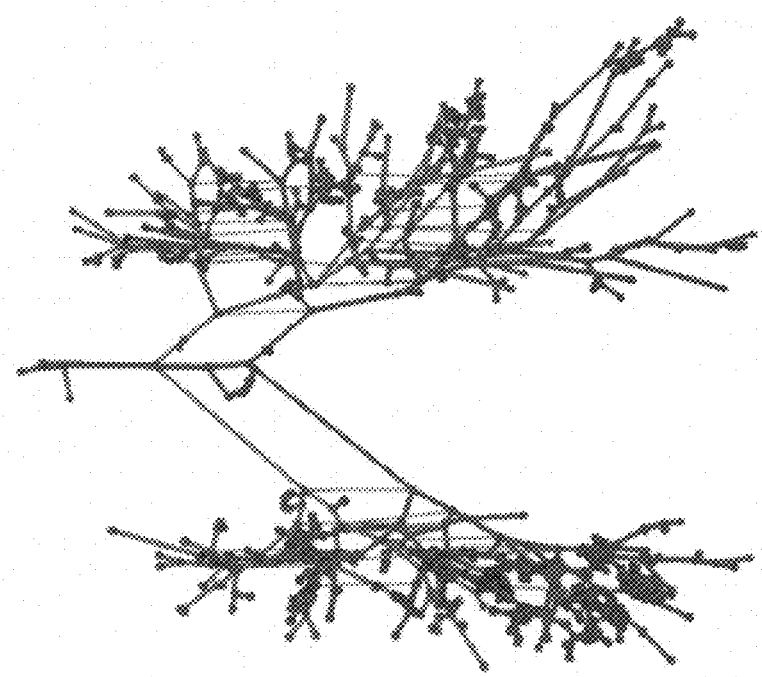
FIG. 5B
FIG. 5A

METHODS AND DEVICES FOR AIRWAY TREE LABELING AND/OR MATCHING

CROSS-REFERENCE(S) TO RELATED APPLICATION(S)

This application claims priority to U.S. Provisional Patent Application Ser. No. 60/568,184, filed May 5, 2004, the entire contents of which (including the appendices) are expressly incorporated by reference.

STATEMENT REGARDING FEDERALLY SPONSORED RESEARCH

The government may own rights in this invention pursuant to National Institute of Health grant number HL-064368.

BACKGROUND

1. Field of the Present Methods and Devices

The present methods and devices relate generally to the fields of labeling and matching. More particular, they relate to labeling graphical representations of trees, such as automated anatomical labeling of human airway trees. They also relate to matching corresponding points of at least two graphical representations, such as automated matching of corresponding branch-points of at least two graphical representations of a tree, such as a human airway tree.

2. Description of Related Art

Lung diseases like lung cancer, emphysema, and cystic fibrosis are a significant cause of disability and premature death in western countries. In North America, for example, fatalities from lung cancer outnumber those from colon, breast, and prostate cancer combined.

Lung imaging plays a crucial role in the diagnosis, study, and treatment of lung disorders as well as in physiological studies concerned with pulmonary functionality. Modern multidetector-row CT scanners (MDCT) provide a wealth of information. Volumetric lung images of the size of several hundred MBytes are not uncommon. The manual analysis of these images is often time-consuming, tedious, and error prone. And with the high volume of scans taken, manual analysis is in many cases not economical.

The quantitative assessment of intrathoracic airway trees is important for the objective evaluation of the bronchial tree structure and function. Functional understanding of pulmonary anatomy as well as the natural course of respiratory diseases like asthma, emphysema, cystic fibrosis, and many others is limited by our inability to repeatedly evaluate the same region of the lungs time after time and perform accurate and reliable positionally corresponding measurements.

Branch-point matching and anatomical labeling are both tedious and error-prone to perform manually. Working with human in-vivo data poses challenges. In-vivo trees deviate from ideal trees because of anatomical variations and because of false-branches introduced by imperfections in the preceding segmentation and skeletonization processes.

Few attempts at automating the branch-point matching process have been made. Pisupati et al. (1996a) and Pisupati et al. (1996b) presented a matching algorithm based on dynamic programming, which was only applied to very similar pairs of canine trees. Pisupati et al. stated that they expect the method to fail on human in-vivo scans. Park (2002) presented a tree-matching method based on an association graph (Pelillo et al. (1999)), but his method was applied only to phantom data and does not tolerate false branches.

Publications about automated anatomical labeling are similarly sparse. Mori et al. (2000) presented a knowledge-based labeling algorithm. The proposed algorithm was only applied to incomplete trees (about 30 branches per tree), and the built-in knowledge base did not incorporate anatomical variations. Additionally, the algorithm is sensitive to missing and added (false) branches. Kitaoka et al. (2002) developed a branch-point labeling algorithm that uses a mathematical phantom as reference. Labels are assigned by matching the target tree against this phantom. The method cannot automatically handle false branches—they have to be pruned manually in a preprocessing step.

Other disclosures concerning an earlier version of the present labeling methods are described in Tschirren et al. (2003), Tschirren et al. (2002a) and Tschirren et al. (2002b).

SUMMARY

Certain embodiments of the present devices include a computer readable medium having machine readable instructions for accessing a first representation of an airway tree of a human subject; accessing a second representation of the airway tree of the human subject; and automatically pruning at least a portion of the first representation.

Other embodiments of the present devices, including embodiments of computer systems, having additional and/or different features are discussed below.

Certain embodiments of the present methods include an automated method comprising accessing a first representation of an airway tree of a human subject; accessing a second representation of the airway tree of the human subject; and automatically pruning at least a portion of the first representation.

Other embodiments of the present methods having additional and/or different features are discussed below.

BRIEF DESCRIPTION OF THE DRAWINGS

The following drawings illustrate by way of example and not limitation. The patent or application file contains at least one drawing executed in color. Copies of this patent or patent application publication with color drawings will be provided by the Office upon request and payment of the necessary fee.

FIG. 2 depicts an algorithm, which is based on a breadth-first search, that may be used to compute $R_v$, discussed in greater detail below.

FIG. 5A is a total view showing the result of using an embodiment of the present matching methods for intra-subject matching, based on an in-vivo TLC and FRC scan. The FRC tree is shown in green and the TLC tree is shown in purple. The matchings are represented by red lines.

FIG. 5B is a detail view of the tree pair shown in FIG. 4A. The false braches near the top center part of the purple tree do not negatively affect the matching result.

FIG. 7A shows the mean±standard deviation of segment length. The trachea was not included because its length varies depending on the start-point of the scan. FIG. 7B shows the standard deviation $\sigma_{100}$ of angle $\phi$ measured from the average spatial orientation of the segment and the spatial orientation of the segment in the individual trees. Note that $\sigma_\phi=0$ for EndLMB_s because of rigid registration (EndLMB_s is always aligned, in this embodiment, with the y-axis.).

FIG. 8A shows variability of difference vector between any two anatomical segments, and standard deviation of the angle between the mean difference vector and the difference vector for the individual trees. FIG. 8B shows standard deviation of angle between direction vectors of any two anatomical segments. Note the relatively constant and moderate values. FIG. 8C shows mean (red)±standard deviation (blue) of segment length ratio for every pair of segments (without trachea). This figure illustrates the great variability and hence the limited value of this measure to embodiments of the present labeling methods. Note that the red line is centered between the blue lines. The apparent asymmetry is a visual illusion.

DESCRIPTION OF ILLUSTRATIVE EMBODIMENTS

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. Thus, an automated method "comprising" accessing a first representation of an airway tree of a human subject; accessing a second representation of the airway tree of the human subject; and (c) automatically pruning at least a portion of the first representation is a method that includes at least these recited steps, but is not limited to only possessing these recited steps.

Similarly, a computer readable medium "comprising" machine readable instructions for accessing a first representation of an airway tree of a human subject; accessing a second representation of the airway tree of the human subject; and automatically pruning at least a portion of the first representation is a computer readable medium that has machine readable instructions for implementing at least these recited steps, but also covers media having machine readable instructions for implementing additional, unrecited steps.

The terms "a" and "an" are defined as one or more than one, unless this application expressly requires otherwise. The term "another" is defined as at least a second or more.

Descriptions of well known processing techniques, components and equipment are omitted so as not to unnecessarily obscure the present methods and devices in unnecessary detail. The descriptions of the present methods and devices, including those in the appendices, are exemplary and non-limiting. Certain substitutions, modifications, additions and/or rearrangements falling within the scope of the claims, but not explicitly listed in this disclosure, may become apparent to those or ordinary skill in the art based on this disclosure.

Figure 1A:
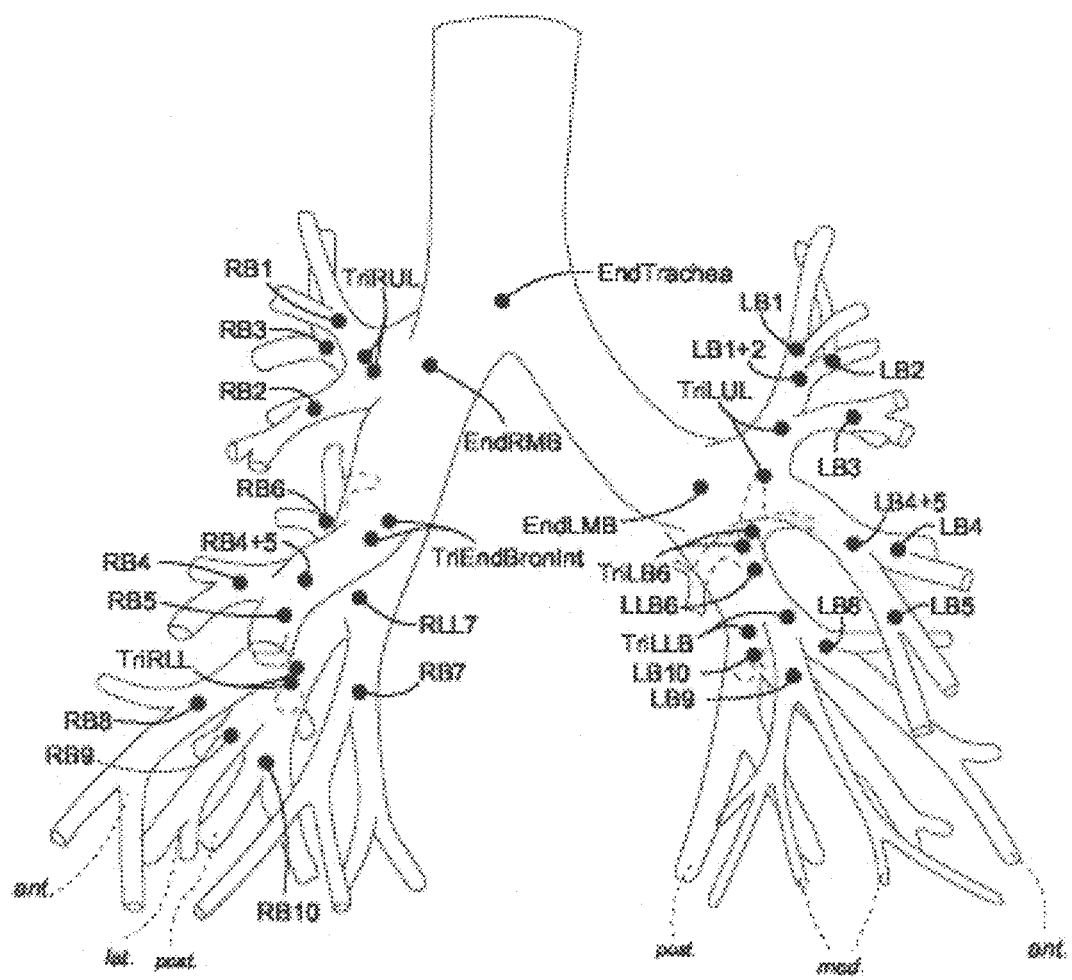
FIG. 1A shows a human airway tree with anatomical labels that are assigned to branch-points and are based on segment names. This figure is based on artwork published in Boyden (1955).
Figure 1B:
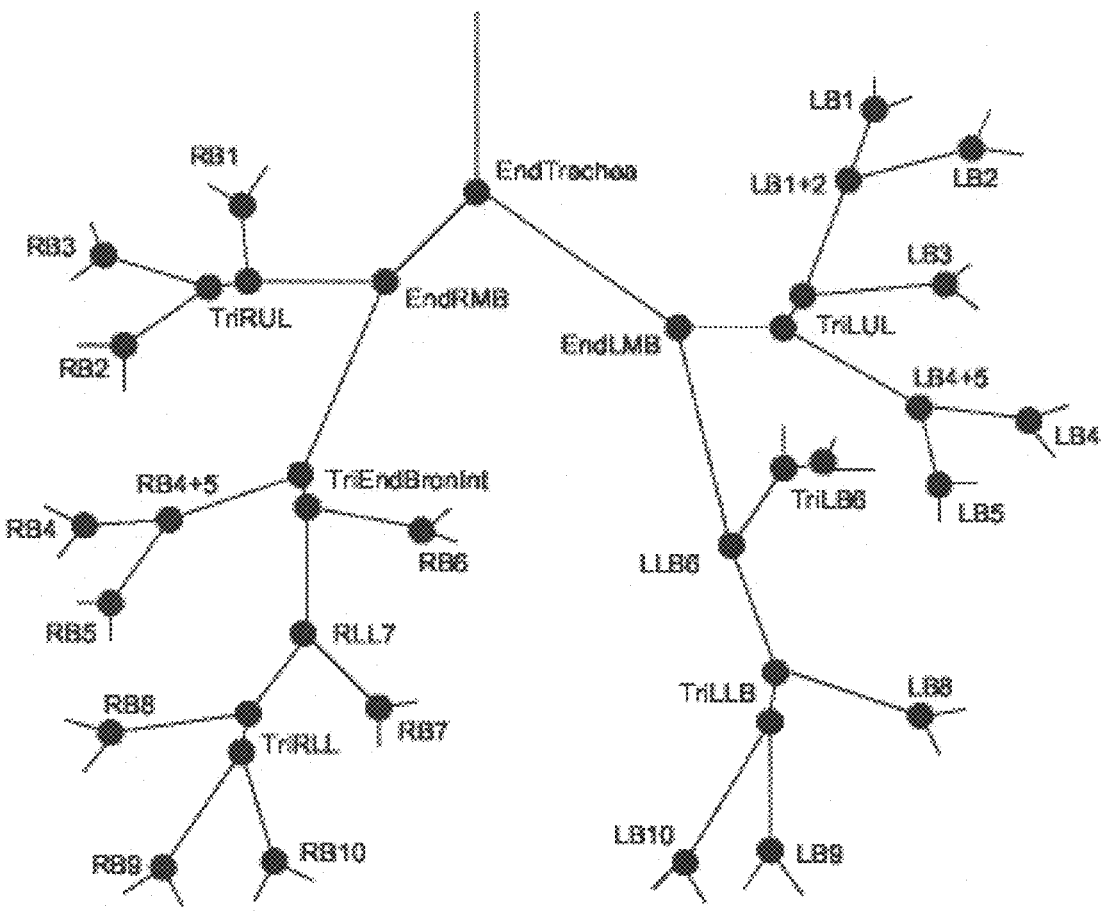
FIG. 1B shows a typical topological relationship of segments (variations are possible between individuals).

Human airway trees show a certain degree of similarity when compared across multiple subjects. The similarities can be observed up to the entry-points into the sub-lobes. This includes all 33 anatomically named segments (see FIG. 1A) that are commonly used in pulmonary physiology Boyden (1955). Beyond that, the branching pattern becomes more random and every human exhibits a different branching pattern, much like fingerprints differ between individuals.

The number of airway-tree branch-points that can be matched depends on the source of the two trees to be compared. In inter-subject matching (trees originating from different subjects), only branch-points associated with the anatomically named segments can be matched. In intra-matching (trees originating from the same subject, e.g., imaged at different lung volumes, or at different points of time), it is possible to match points beyond the anatomically named ones.

Prior to either matching or labeling, an airway tree may be segmented using any suitable technique from suitable data. For example, segmentation may be accomplished on volumetric computed tomography (CT) images using processes such as those described in, e.g., (a) Chapter 2 of Appendix 1 of the provisional application to which this application claims priority and incorporates by reference, or (b) Appendix 4 of the provisional application to which this application claims priority and incorporates by reference (to the extent the two descriptions differ). The segmented airway tree may then be skeletonized using any suitable technique, such as the technique as disclosed, for example, in Palagyi et al. (2003).

Branch-points may then be detected in the skeletonization result and the tree may be represented as a directed acyclic graph (DAG). This DAG may be used as input data for both present branch-point matching and anatomical labeling methods.

In one respect, the present devices may be characterized as a computer readable medium comprising machine readable instructions for: (a) accessing a first representation of an airway tree of a human subject; (b) accessing a second representation of the airway tree of the human subject; and (c) automatically pruning at least a portion of the first representation. In one respect, the present methods may be characterized as an automated method comprising: (a) accessing a first representation of an airway tree of a human subject; (b) accessing a second representation of the airway tree of the human subject; and (c) automatically pruning at least a portion of the first representation. The representations that are accessed consistent with such devices and methods may take the form of data.

In another respect, the present devices may be characterized as a computer readable medium comprising machine readable instructions for: (a) accessing a first representation, the first representation including a segmented, skeletonized representation of an airway tree at a first lung volume of a human subject; (b) accessing a second representation, the second representation including a segmented, skeletonized representation of the airway tree at a second lung volume of a human subject; and (c) automatically pruning at least a portion of the first representation. In another respect, the present methods may be characterized as an automated method comprising: (a) accessing a first representation, the first representation including a segmented, skeletonized representation of an airway tree at a first lung volume of a human subject; (b) accessing a second representation, the second representation including a segmented, skeletonized representation of the airway tree at a second lung volume of a human subject; and (c) automatically pruning at least a portion of the first representation.

In one respect, embodiments of the present branch-point matching methods may be characterized as having the following steps, which can be performed automatically: delete (prune) spurious branches from input trees; align the input trees by performing a rigid registration; find and match major branch-points; and match sub-trees underneath major branch-points, one pair of sub-trees at a time.

In another respect, embodiments of the present branch-point matching methods may be characterized as having the following steps, which can be performed automatically: delete (prune) spurious branches from input trees; find major branch-points (e.g., the carina and the end-points of the two main bronchi); rigid registration based on major branch points found (input trees are aligned based on the major branch-points found in the previous step); find remaining major branch-points; match remaining major branch-points; and match sub-trees (remaining branch-point correspondences may be found by matching, e.g., only one pair of sub-trees at a time).

Embodiments of both the present branch-point matching and the anatomical labeling methods may be based on matching hierarchical structures (mathematical graphs) using association graphs Pelillo (1999). Using association graphs for finding graph isomorphisms is a well known technique that was introduced more than 20 years ago Ballard and Brown (1982) refined the method, allowing it be used on hierarchical structures, such that topological and inheritance relationships were preserved.

An association graph is an auxiliary graph structure derived from the two graph structures to be matched. A graph $G=(V, E)$ comprises a set of vertices V and a set of edges E. For two graphs $G_1$ and $G_2$, an association graph $G_{ag}=(V_{ag}, E_{ag})$ consists of the vertices $V_{ag}=V_1 \times V_2$. Thus, it contains a vertex for every possible pair of vertices in $G_1$ and $G_2$. Two vertices in $G_{ag}$ are connected with an edge if and only if the corresponding vertices in $G_1$ and $G_2$ stand in the same relationship to each other (e.g., inheritance relationship, topological distance, etc.). The maximum clique in the association graph (the biggest sub-set of vertices where every pair of vertices is connected by an edge) corresponds to the maximal subtree isomorphism. Each vertex contained in the maximum clique represents a pair of matching vertices in the original graphs. It has been shown (Garey and Johnson, 1979) that the problem of finding the maximum clique is an NP-complete problem. No method is known to exist that can efficiently find the maximum clique in a graph with a high number of vertices and edges. However, embodiments of the present methods may reduce the time required to match two normal sized in-vivo trees to about 1 to 3 seconds.

Pelillo et al. (1999) use path length and level difference (generation number) as a measure of equivalence when adding edges to the association graph. This is "hard" measure in the sense that only topologically identical sub-trees can be matched. In contrast, embodiments of the present methods use a measure of equivalence that incorporates tolerances, allowing topological differences between the target trees, and consequently making the process robust against false branches, which are commonly observed in the segmentation (due, for example, to leaks) and skeletonization (due, for example, to naturally occurring "bumps" along the airway wall) result of in vivo data.

Reducing Computing Time

Computing the maximum clique is an NP-complete problem. For example, attempting to match two trees of 200-300 vertices each in a naive way could require computing time on the order of hours. Reducing the problem size will decrease this time. Such a reduction could be achieved in different ways. For example, the overall problem size could be reduced, or the problem could be split into a greater number of smaller sub-problems. Some embodiments of the present matching methods use a combination of both of these approaches.

In this regard, the overall problem size may be reduced by pruning out very short (and mostly spurious) terminal branches from the input trees. Next, the input trees (e.g., two input trees) undergo a rigid registration to bring potentially matching branch-points geometrically close to each other and to allow the imposition of a distance restriction when building the association graph. With such an approach, only geometrically close branch-points are considered as possible matches. Next, the trees may be divided into sub-trees, and only two relatively small sub-trees may be matched at a time. A more detailed discussion of one manner of carrying out these general steps is now provided.

Pruning

Figure 3C:
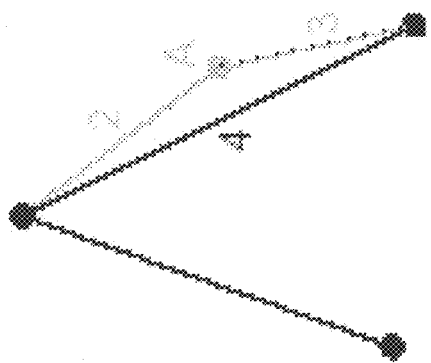
FIG. 3C shows the result of pruning the false branch shown in FIG. 3A, and replacing the vertex from which it extended with an edge.
Figure 3B:
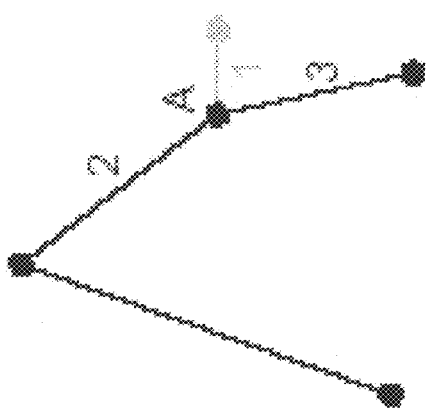
FIG. 3B shows that edge 1 in FIG. 3A is a false branch.
Figure 3A:
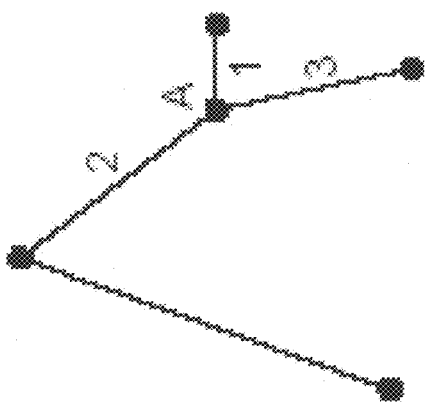
FIG. 3A shows a portion of a segmented, skeletonized airway tree before pruning.

Pruning short terminal branches comprises, in some embodiments of the present matching methods, two steps: deleting terminal branches that are shorter than a pre-defined threshold $l_{th}$ and deleting vertices that have only one out-edge and replacing the in-edge and out-edge with one single edge (stated another way, deleting vertices that have only one remaining out-edge and connecting parent- and child-vertices directly). FIGS. 3A-3C illustrate an embodiment of these steps. FIG. 3A shows a portion of a segmented, skeletonized airway tree before pruning. FIG. 3B shows that edge 1 is a terminal edge and has a length $l<l_{th}$, and the same is identified as a false branch and deleted. In FIG. 3C, the false branch no longer appears, and vertex A is found to have only one out-edge. Consequently, vertex A and edges 2 and 3 are deleted and edge 4 is inserted. In embodiments of the present matching methods, the pruning is applied two times in a sequence for every tree. Thus, a maximum of two airway-generations is deleted from the periphery of the trees.

Rigid Registration

In some embodiments of the present matching methods, a rigid registration may be performed such that the carinas of the input trees are superimposed and the angles between the corresponding main bronchi of the two trees are minimized. The carina is the first main branch-point of the airway tree where the trachea splits into the two main bronchi. The carina and the left and right bronchus of each input tree may be identified first, as follows. For every tree a depth first search may be performed, which labels every edge e with the minimum and maximum values of the x, y, and z positions of all vertices that are situated topologically underneath e, designated as $x_{min}(e), x_{max}(e), \ldots, z_{max}(e)$. The number of vertices found topologically underneath e is recorded as well, designated as $N(e)$.

The spatial extents $\Delta_x(e)=x_{max}(e)-x_{min}(e)$, $\Delta_y(e)=y_{max}(e)-y_{min}(e)$, and $\Delta_z(e)=z_{max}(e)-z_{min}(e)$ can now be computed for every edge e. Next, a breadth first search may be performed starting from the root of the tree. The carina may be identified as the first vertex that is encountered with $\Delta xyz=\max\{\Delta_x(e), \Delta_y(e), \Delta_z(e)\} \leq 50$ millimeters (mm) and $$\frac{N(e)}{|V|} \geq 0.1$$

0.1 for both of its out-edges. Similarly, the branch-points at the end of the two main bronchi may be found by finding the next two vertices after the carina that satisfy the same conditions.

Figure 4B:
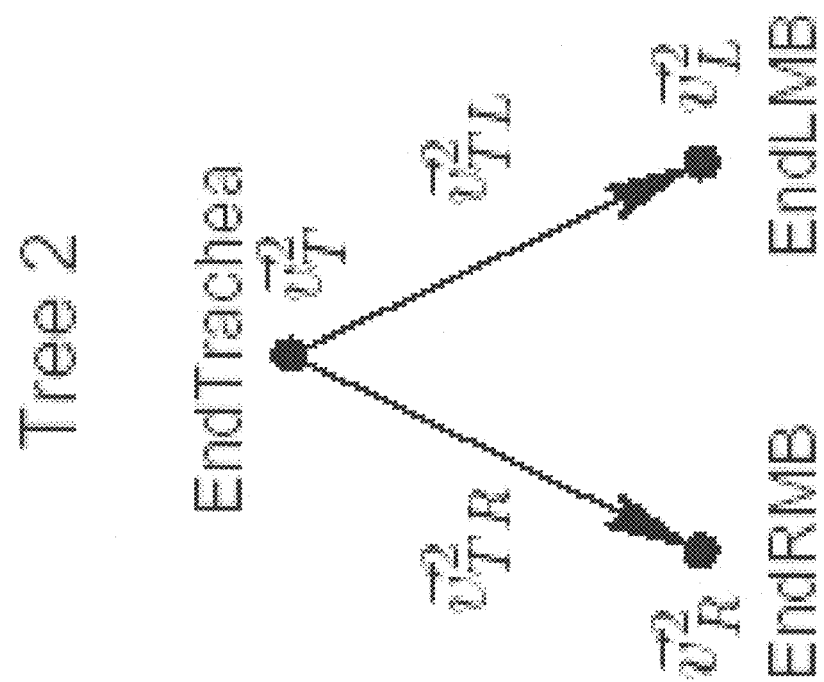
FIGS. 4A and 4B show suitable nomenclature for rigid registration. The depicted anatomical names correspond to names in FIG. 1B.
Figure 4A:
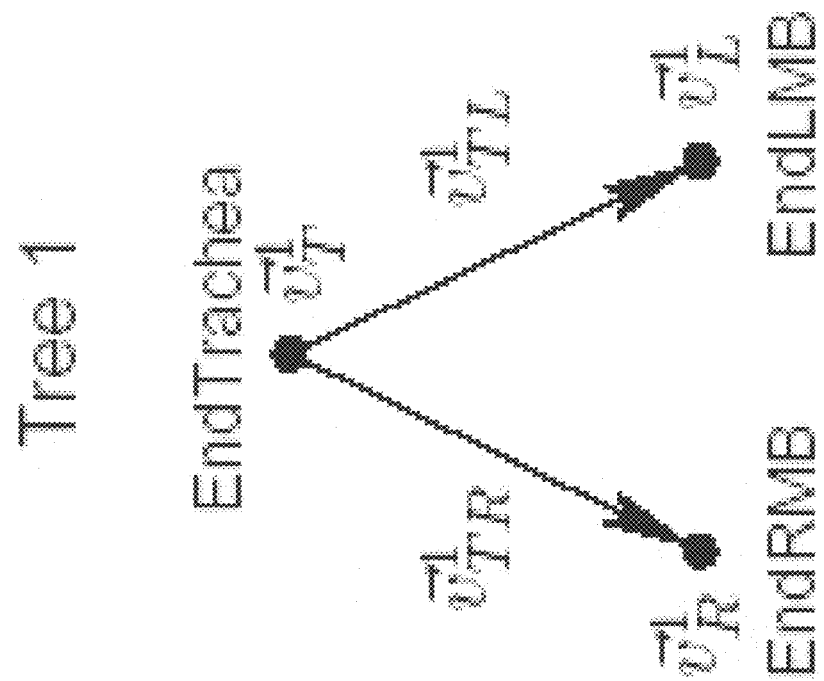

The notation in the following equations refers to FIGS. 4A and 4B. The rotation angles are the x, y, and z-axes, $\phi_{yz\,avg}$, $\phi_{xz\,avg}$, and $\phi_{xy\,avg}$, respectively, computed with $$\varphi_{yz\,avg} = \left[\varphi_{diff}\left(\tan^{-1}\frac{\vec{v}^1_{TR_y}}{\vec{v}^1_{TR_z}}, \tan^{-1}\frac{\vec{v}^2_{TR_y}}{\vec{v}^2_{TR_z}}\right) + \varphi_{diff}\left(\tan^{-1}\frac{\vec{v}^1_{TL_y}}{\vec{v}^1_{TL_z}}, \tan^{-1}\frac{\vec{v}^2_{TL_y}}{\vec{v}^2_{TL_z}}\right)\right]/2$$

$$\varphi_{xz\,avg} = \left[\varphi_{diff}\left(\tan^{-1}\frac{\vec{v}^1_{TR_x}}{\vec{v}^1_{TR_z}}, \tan^{-1}\frac{\vec{v}^2_{TR_x}}{\vec{v}^2_{TR_z}}\right) + \varphi_{diff}\left(\tan^{-1}\frac{\vec{v}^1_{TL_x}}{\vec{v}^1_{TL_z}}, \tan^{-1}\frac{\vec{v}^2_{TL_x}}{\vec{v}^2_{TL_z}}\right)\right]/2$$

$$\varphi_{xy\,avg} = \left[\varphi_{diff}\left(\tan^{-1}\frac{\vec{v}^1_{TR_x}}{\vec{v}^1_{TR_y}}, \tan^{-1}\frac{\vec{v}^2_{TR_x}}{\vec{v}^2_{TR_y}}\right) + \varphi_{diff}\left(\tan^{-1}\frac{\vec{v}^1_{TL_x}}{\vec{v}^1_{TL_y}}, \tan^{-1}\frac{\vec{v}^2_{TL_x}}{\vec{v}^2_{TL_y}}\right)\right]/2$$

where the function $\phi_{diff}(\phi_1, \phi_2)$ finds the shorter of the two possible difference angles between $\phi_1$ and $\phi_2$ and is defined by:

$$\varphi_{diff}(\varphi_1, \varphi_2) = \begin{cases} \varphi_1 - \varphi_2, & \text{if } |\varphi_1 - \varphi_2| \leq \pi \\ 2\pi = \varphi_1 - \varphi_2, & \text{if } \varphi_1 - \varphi_2 > \pi \\ 2\pi = \varphi_1 - \varphi_2, & \text{if } \varphi_1 - \varphi_2 < \pi \end{cases} \quad (3.2)$$

The 3D transformation of the vertex coordinates can be written in the standard matrix representation (Foley (1990)) as $$[x_T, y_T, z_T]' = T \cdot [x, y, z]' \quad (3.3)$$

where $[x, y, z,]$ is the original vertex coordinate and $[x_T, y_T, z_T]$ is the transformed vertex coordinate. The transformation matrix M is defined by $$M = \begin{bmatrix} 1 & 0 & 0 & \vec{v}^1_{T_x} \\ 0 & 1 & 0 & \vec{v}^1_{T_y} \\ 0 & 0 & 1 & \vec{v}^1_{T_z} \\ 0 & 0 & 0 & 1 \end{bmatrix} \cdot R_z \cdot R_x \cdot R_y \begin{bmatrix} 1 & 0 & 0 & \vec{v}^2_{T_x} \\ 0 & 1 & 0 & \vec{v}^2_{T_y} \\ 0 & 0 & 1 & \vec{v}^2_{T_z} \\ 0 & 0 & 0 & 1 \end{bmatrix} \text{ with} \quad (3.4)$$

-continued $$R_z = \begin{bmatrix} \cos\varphi_{xy\,avg} & -\sin\varphi_{xy\,avg} & 0 & 0 \\ \sin\varphi_{xy\,avg} & \cos\varphi_{xy\,avg} & 0 & 0 \\ 0 & 0 & 1 & 0 \\ 0 & 0 & 0 & 1 \end{bmatrix} \quad (3.5)$$

$$R_x = \begin{bmatrix} 1 & 0 & 0 & 0 \\ 0 & \cos\varphi_{yz\,avg} & -\sin\varphi_{yz\,avg} & 0 \\ 0 & \sin\varphi_{yz\,avg} & \cos\varphi_{yz\,avg} & 0 \\ 0 & 0 & 0 & 1 \end{bmatrix}$$

$$R_y = \begin{bmatrix} \cos\varphi_{xz\,avg} & 0 & \sin\varphi_{xz\,avg} & 0 \\ 0 & 1 & 0 & 0 \\ -\sin\varphi_{xz\,avg} & 0 & \cos\varphi_{xz\,avg} & 0 \\ 0 & 0 & 0 & 1 \end{bmatrix}$$

Matching (3.1)

In some embodiments of the present matching methods, matching of the remaining branch-points (those other than the carina and the end-points of the two main bronchi) may be performed in multiple (e.g., two) steps to help reduce computing time. For example, first only major branch-points (which are generally branch-points that are a parent of sub-trees having substantial size, such as those with a spatial extent of $\Delta xyz=30$ mm) are matched. This requires minimal computing time because there are, on average, only 20-30 major branch-points identified per tree. Then, starting from pairs of matched major branch-points, sub-trees are matched, only one pair of sub-trees at a time. Prior to matching two sub-trees, a simplified rigid registration may be executed by translating one of the two sub-trees such that the root points of the sub-trees are superimposed.

In other words, with respect to the major branch-point matching, in some embodiments of the present matching methods, major branch-points other than the carina and the end-points of the two main bronchi may be identified using the same techniques discussed above with respect to identifying the carina and the end-points of the two main bronchi during the rigid registration. The only difference is that the threshold for the spatial extent is lowered to $\Delta xyz=30$ mm and no restriction for the minimal number of vertices in a sub-tree is used.

Building Association Graph

In some embodiments of the present methods, the association graph is built in keeping with a goal of having its maximum clique represent as many valid matches as possible. One could add a vertex to the association graph for every possible pair of vertices in the original trees and connect association graph vertices with edges if they represent the exact same relationships between the respective vertices in the two input trees. However, considering the average number of 200 to 300 vertices in the input trees, this approach could produce a huge association graph, and the time to find the maximum clique will rise beyond practical values. Furthermore, such an approach does not allow for tolerances and will not tolerate false branches well. In some embodiments of the present methods, it is beneficial to keep the size of the association graph small and make the overall matching process tolerant against false branches.

The segmentation and skeletonization processes may leave some false (extraneous, anatomically non-existing) branches in the tree. Trees scanned at a high lung volume are more prone to such branches than trees scanned at a low lung volume. It should not be expected that a false branch will simultaneously occur in both input trees (e.g., when intra-subject trees are at issue) and at the same location.

A false branch does not change the inheritance relationship of any two vertices in the graph. Siblings stay siblings, parents stay parents of their respective children and vice-versa. However, the topological distance between some vertices does change when a false branch is introduced.

Vertex Relationship Array

In embodiments of the present methods, the inheritance relationship and the topological distance between any two vertices for each input tree (e.g., two input trees) is known prior to building the association graph. To ascertain these properties, the two-dimensional vertex relationship array $R_v$ of dimension N×N is computed, where N stands for the number of vertices in the associated tree. The cell $R_v(s, t)$ of $R_v$ contains the inheritance relationship $r_{s,t} \in$ {PARENT, CHILD, SIBLING, N/A} and the topological distance $d_{s,t} \in N$ between the source vertex s and the target vertex t, with $(r_{s,t}=N/A, d_{s,t}=0) \Leftrightarrow s=t$. For s≠t no inheritance relationships except PARENT, CHILD, and SIBLING are possible and $r_{s,t} \geq 1$. If vertex n is not a direct descendant of vertex m and m is not a direct descendant of n then $r_{n,m}=r_{m,n}=$SIBLING. No "COUSINS", "NEPHEWS" or similar are assigned. In this regard, embodiments of the present methods and devices may be characterized as an automated method comprising, or a computer readable medium comprising machine readable instructions for, respectively, (a) accessing a first representation of an airway tree of a human subject, the first representation including vertices; (b) accessing a second representation of the airway tree of the human subject, the second representation including vertices; and (c) building a tree association graph, where the building includes assigning vertices to the tree association graph such that no inheritance relationships other than parent, child, or sibling exist among the vertices. Using this inheritance model simplifies the handling of trifurcations that may occur in the form of two bifurcations that follow each other immediately, and that may occur in different order in the second tree. In either case the vertices that are topologically below the trifurcation stay siblings and thus can still be matched. Further, the presence of false branches does not disturb the inheritance relationship. Consequently, it becomes possible to tolerate false branches to a certain degree—a benefit when matching in-vivo trees.

Figure 2:
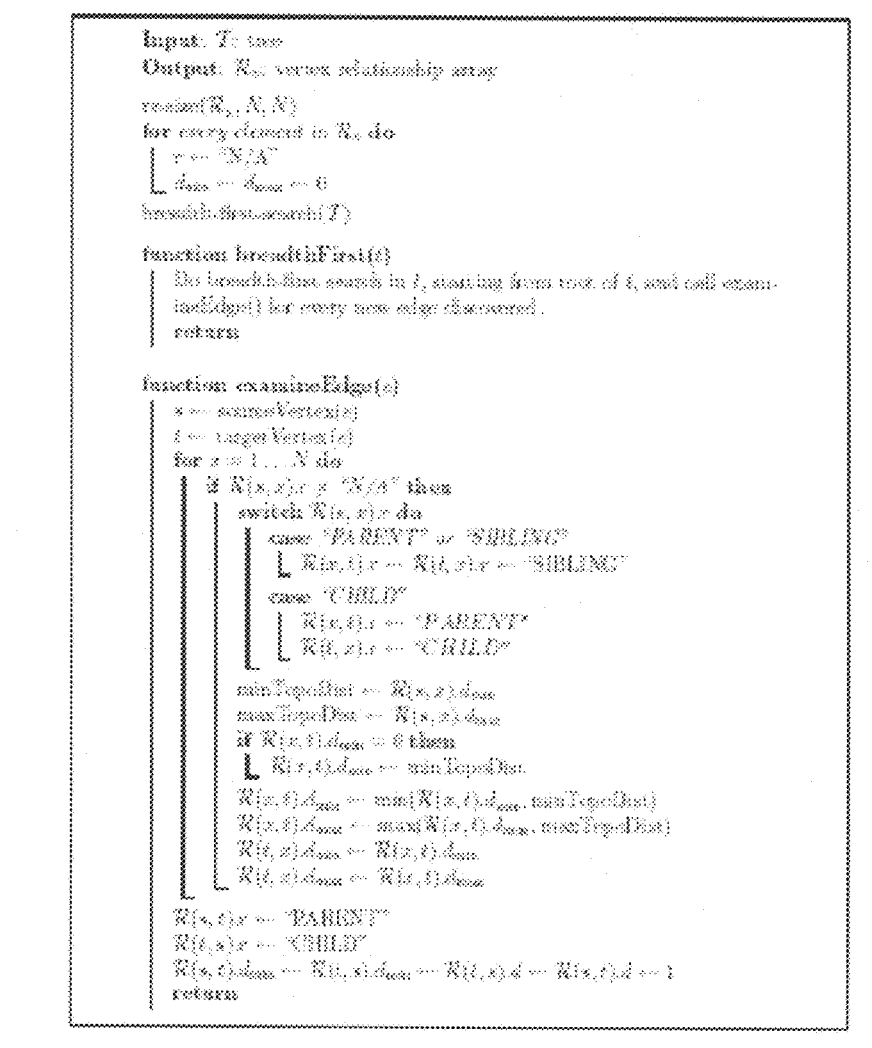

$R_v$ may be computed with Algorithm 1 depicted in FIG. 2, which is based on a breadth-first search. It should be noted that $d_{min}=d_{max}$ for some embodiments of the present branch-point matching methods, and for some embodiments of the present anatomical labeling methods it may be $d_{min} \neq d_{max}$.

In some embodiments of the present methods, vertices are only added to the association graph if the two corresponding vertices in the trees to be matched are not farther than $d_{max}$ apart. The value of $d_{max}$ may be set to 40 mm for matching the major branch-points, and to 15 mm for matching the sub-trees (see below).

Thus, embodiments of the present methods and devices may be characterized as an automated method comprising, or a computer readable medium comprising machine readable instructions for, respectively, (a) accessing a first representation of an airway tree of a human subject, the first representation including vertices; (b) accessing a second representation of the airway tree of the human subject, the second representation including vertices; and (c) building a tree association graph, where the building includes determining whether two possible vertices of the tree association graph have a topological distance that falls within a range of acceptable topological distances.

In some embodiments of the present methods, there are guidelines for the placement of edges in the association graph. For example, consider two vertices in the association graph, $v_{assoc1}$ and $v_{assoc2}$. In some embodiments, if $v_{assoc1}$ represents a match between vertex $v_{1a}$ in tree 1 and $v_{2a}$ in tree 2, and if $v_{assoc2}$ represents a match between vertex $v_{1b}$ in tree 1 and $v_{2b}$ in tree 2, then $v_{assoc1}$ and $v_{assoc2}$ are only connected with an edge if the following are true:

the inheritance relationship from $v_{1a}$ to $v_{1b}$ is identical to the inheritance relationship from $v_{2a}$ to $v_{2b}$;

the topological distance between $v_{1a}$ and $v_{1b}$ and the topological distance between $v_{2a}$ and $v_{2b}$ differ by at most ±2;

the Euclidean distance between $v_{1a}$ and $v_{1b}$ and the Euclidean distance between $v_{2a}$ and $v_{2b}$ differ by at most 20%; and the angle between the two vectors $v_{1a}-v_{1b}$ and $v_{2a}-v_{2b}$ is at most 1 radian.

These factors minimize the size of the association graph and consequently speed up the matching process. The tolerance for topological distances makes it possible to allow false branches to some degree (e.g., such as the false branches not eliminated by pruning).

Finding Maximum Clique

A number of exact algorithms as well as heuristic approximation techniques have been presented for solving the maximum clique problem (see Carraghan et al. (1990); Ostergard (2002); and Pardalos et al. (1999)). For most large problems an algorithm based on a heuristic methods is the only reasonable choice in order to keep the computing time within practicable limits. However, a heuristic method does not guarantee an optimal solution—something an exact algorithm can do. In embodiments of the branch-point matching methods, the branch-point matching problem can be divided into a number of relatively small sub-problems as discussed below. For that reason, an exact maximum clique algorithm is applied in certain embodiments. Algorithm 2 (based on Carraghan et al. (1990)) in Table 1 below, which is a non-weighted (or un-weighted) maximum clique algorithm, may be used in this regard. The runtime for the matching process amounts to 1 to 3 seconds for two trees containing 200 to 300 branch-points each (measured on a 1.2 GHz AMD Athlon™ single CPU system).

TABLE 1

Algorithm 2

Input: C: Graph with set of vertices V and set of edges E.

Output: C: Maximum unweighted clique.

TABLE 1-continued

Algorithm 2

```
 1  max ← 0
 2  clique ← ∅
 3  tmp_clique ← ∅
 4  _maxClique(V, 0)
 5  return clique
 6  function _maxClique (U, size)
 7      if U = 0 then
 8          if (size > max) then
 9              max ← size
10              clique ← tmp_clique
11          return
12      while U ≠ ∅ do
13          if size + U ≤ max then
14              return
15          i ← min{j v_j ∈ U}
16          U ← U\{v_i}
17          _maxClique(U∩neighbors(v_i), size +1)
18      return
```

Implementation

In some embodiments of the present methods, the graph-related parts may be realized with the help of the Boost Graph Library, Siek et al. (2002). The complete matching algorithm may be implemented as a command-line application written in ANSI C++ (e.g., one example of machine-readable instructions). Such a program can take two XML tree files as input and can output an XML tree-matching file.

XML is a suitable platform because of the expandability of XML-based files and because powerful parsers are readily available. Two different data files were designed:

The tree file contains all tree-related data except the original gray-scale image and volumetric segmentation result. Information about topology and geometry are stored, as well as the results of all quantitative measurements. The tree file can hold trees with disconnected parts and trees containing loops, if needed. Anatomical labels, work status (information about what processing steps have been performed on the tree), and text-based notes provided by the user can also be stored; and The tree-matching file contains information about matching branch-points, segments, and lobes between two airway-trees. As with the tree file, the tree-matching file can also hold information about the work status and it can hold text notes.

C++ and Python libraries were developed for accessing these files. Providing these libraries has several advantages: data access is simplified and new applications can be added with relative ease; data-integrity is guaranteed because all read and write operations are done through the libraries; and cross-platform operability is assured by using standardized language features only, and by using cross-platform third-party libraries only.

Pages 142-171 (beginning with section 8.3.4 of page 142) of Appendix 1 of U.S. Provisional Patent Application Ser. No. 60/568,184, which pages are incorporated by reference in this application, describe one embodiment of the two file formats and the C++ and Python libraries that can come with them.

Modularity

The processing steps described in this disclosure may be integrated into separate modules. Each module may be specialized to a specific task and data exchange may be standardized as described above. Individual modules can be exchanged or new modules can be added as needed. Specialized tools can be built by combining different modules into a higher-level system.

Modules have been developed to carry out aspects of this disclosure that were command-line based and parameterized through command-line parameters. Integration into scripts may be currently be achieved via a command-line interface (e.g., with the 'os.system( )' command in Python). Integration into a system based on standardized binary modules like the one described in pages 141-143 of Appendix 1 of U.S. Provisional Patent Application Ser. No. 60/568,184, which pages are incorporated by reference in this application, may be realized by replacing the thin command-line interface layer with the new interface code.

All modules may be implemented in standard ANSI C++ for cross-platform operability. Portable and freely available third-party libraries may be used.

Results

FIGS. 5A and 5B show a result of using an embodiment of the present matching methods for intra-subject matching. The run time for matching two full-sized in-vivo trees (200-300 branch-points each) was about 1 to 2 seconds, measured on a single AMD Athlon™ CPU running at a clock rate of 1.2 GHz.

Specifically, validation of an embodiment of the present branch-point matching methods was performed with in-vivo data sets. The accuracy of the embodiment was evaluated by comparing the automated results against an independent standard that was based on the hand-matching result provided by several independent human experts.

Independent Standard

Scans from a total of 17 subjects, 10 healthy and 7 diseased, were available. Each subject was scanned twice, one scan at functional residual capacity (FRC, 55% lung-volume), and one scan at total lung capacity (TLC, 85% lung-volume). In each volume the airway-tree was segmented and skeletonized by automated methods, and the graph representation of the airway-trees was then available for matching. An interactive computer program was developed that allowed human experts to perform the tree-matching. Each pair of FRC/TLC trees was matched independently by three different human experts. For each tree-pair, the FRC and the TLC tree originated from the same subject. It was therefore possible to match branch-points beyond the anatomically named points. A match between two branch-points was only taken as a reference if a majority of human observers (at least two out of three) agreed on it.

Automated Method

The embodiment of the present branch-point matching methods was run on all 17 tree pairs. The input trees were taken from the skeletonization program "as is"; no manual pre-processing (e.g., pruning) took place. All 17 tree pairs were matched with the automated program using the same standard parameters. No hand-adjusting of parameters took place.

For every tree pair the result of the automated matching program was validated against the independent reference described in the previous sub-section. Table 2 lists the validation results for the matching algorithm:

TABLE 2

|  | 10 subjects in vivo normal | 7 subjects in vivo diseased | Total |
| --- | --- | --- | --- |
| Total reference matches | 193 | 211 | 404 |
| Verified computer matches | 124 | 130 | 254 |
| correct | 113 (91.1%) | 123 (94.6%) | 236 (92.9%) |
| incorrect | 11 (8.9%) | 7 (5.4%) | 18 (7.1%) |

TABLE 2-continued

|  | 10 subjects in vivo normal | 7 subjects in vivo diseased | Total |
|---|---|---|---|
| Computer matches not in reference | 79 | 40 | 119 |
| Reference matches not in computer matches | 80 | 88 | 168 |

In the intra-subject branch-point matching, 92.9% of the verifiable matches agreed with the independent standard. It is interesting to compare the 7.1% incorrect matches with the intra-observer disagreement. On average, 7.5% of the branch-point correspondences identified by the human experts disagreed with each other. For some tree-pairs the human expert disagreement was as high as 28.6%.

While the embodiments of the present matching methods (and devices) have been discussed in the context of the human airway tree, those of ordinary skill in the art will understand that they are also applicable to matching aspects (such as vertices) of any other artificial or natural tree structure.

Next we turn to some embodiments of the present anatomical labeling methods.

Assigning anatomical labels makes it possible to match airway tree across different subjects. This allows, for example, physiological studies where, across a population, the average change of airway geometry during the breathing cycle is of interest. Having anatomical labels assigned to an airway tree also makes it possible to identify lobes and sub-lobes, which is crucial for surgical planning.

In some embodiments of the present methods, anatomical labels are assigned by matching the target tree against a pre-labeled tree that represents a population average and contains information about the typical geometrical and topological variability in human airway trees. Because of false branches an anatomical segment may consist of more than one edge in the graph representation of the airway tree that is to be labeled. For that reason, labels may be assigned to the respective endpoint (branch-point) of the segment. An anatomical segment can have only one endpoint, and a branch-point can only be the endpoint of one anatomical segment. Consequently, this approach allows for an unambiguous labeling that is independent of the number of graph-edges that make up one anatomical segment.

In general, the labeling of some embodiments of the present labeling methods is performed by matching the target tree against a population average. The population average may be built from a number of airway trees that are hand-labeled by one or more human experts. The population average may incorporate the variability that can typically be observed across subjects of the population.

Population Average

The population average is a data base that contains a reference-airway tree with anatomical labels. It also contains the mean values for various geometrical measures, as well as information about the typical geometrical and topological variations across the population. The following sub-sections describe the details about how the population average may be built according to some embodiments of the present labeling methods.

Notation

Figure 6:
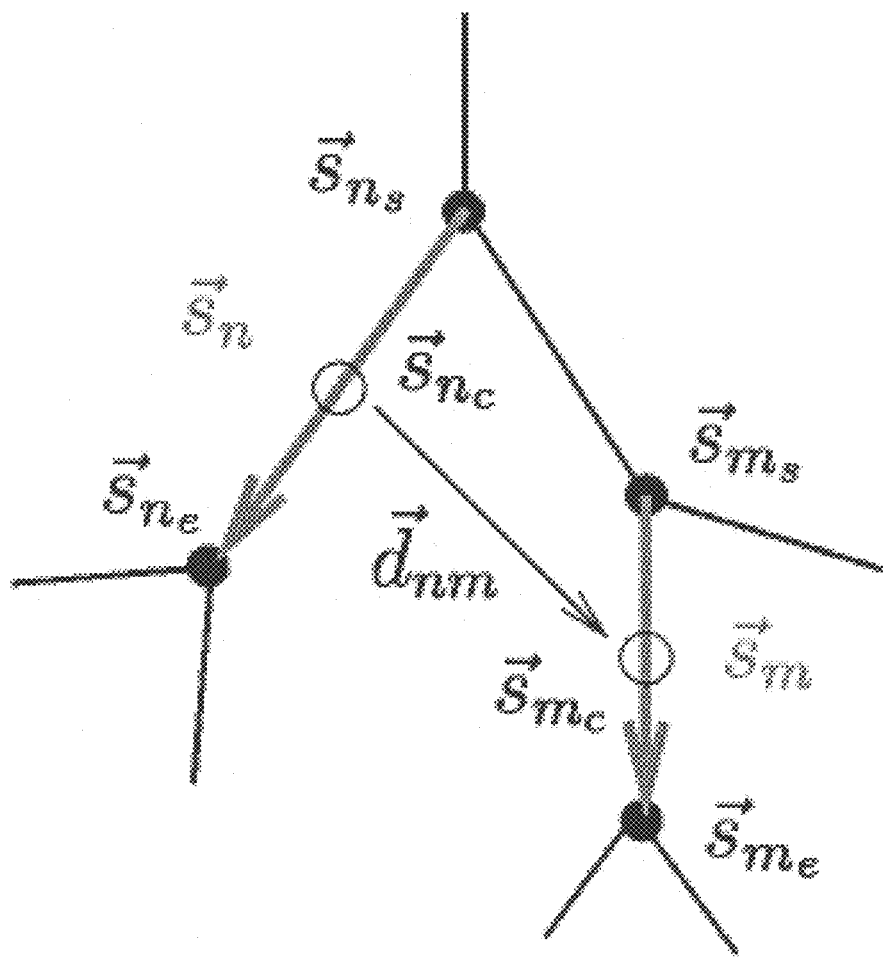
FIG. 6 shows an example of the notation that can be used in the population average described below.

A vector notation may be used for computing the population average. In FIG. 6, the vector $\vec{s}_n$ defines the orientation and length of segment n, and $\vec{s}_m$ does the same for segment m. Every segment has a start point, a center point, and an end point, designated by the subscripts s, c, and e, respectively. The difference vector $\vec{d}_{nm} = \vec{s}_{mc} - \vec{s}_{mc}$ is defined by the two center points.

Rigid Registration

The population average will contain information about the absolute spatial orientation of segments and the spatial relation between pairs of segments. This information can only be computed relative to a predefined reference frame. The coordinates of the tree vertices are defined in a Cartesian coordinate system. Trees used for computing the population average undergo a rigid registration such that the carina lies in the origin of the coordinate system, the left main bronchus is aligned with the z-axis of the coordinate system (with the end of the left main bronchus pointing into positive z direction), and the plane defined by the two main bronchi is congruent with the x-z plane of the coordinate system (this also makes possible the measurement of absolute positions of segments, though this information is not contained in the embodiment of the population average discussed because it can be replaced with relative spatial measurements). A 3D transformation of the vertex coordinates as it is used within the embodiment of the present branch-point matching methods discussed above may be used.

Information Contained in Population Average

Two different classes of knowledge are contained in the population average. The first class comprises pre-knowledge related to single segments. The second class comprises pre-knowledge about the relationship between pairs of segments.

For the single segment pre-knowledge, the following parameters are recorded:

Segment length—for, e.g., every segment the absolute length is computed. The population average contains the mean $\mu_1$ and standard deviation $\sigma_1$ of the measured values, separately listed for, e.g., every anatomically named segment.

Spatial orientation—for, e.g., every anatomically named segment the mean vector $\vec{\mu}_{SO}$ is computed from T hand-labeled input trees with $$\vec{\mu}_{SO} = \frac{\sum_{i=0}^{T-1} \vec{s}_n}{T} \tag{4.1}$$

and the unit vector of $\vec{\mu}_n$ is recorded in the population average. Furthermore, the average variation from $\vec{\mu}_n$ is found by computing the standard deviation of the angle between $\vec{\mu}_n$ with $$\sigma_{SO} = \sqrt{\frac{1}{T-1} \sum_{i=0}^{T-1} \left( \cos^{-1} \frac{\vec{S}_n \cdot \vec{\mu}_{SO}}{|\vec{S}_n| \cdot |\vec{\mu}_{SO}|} \right)^2} \tag{4.2}$$

Figure 7B:
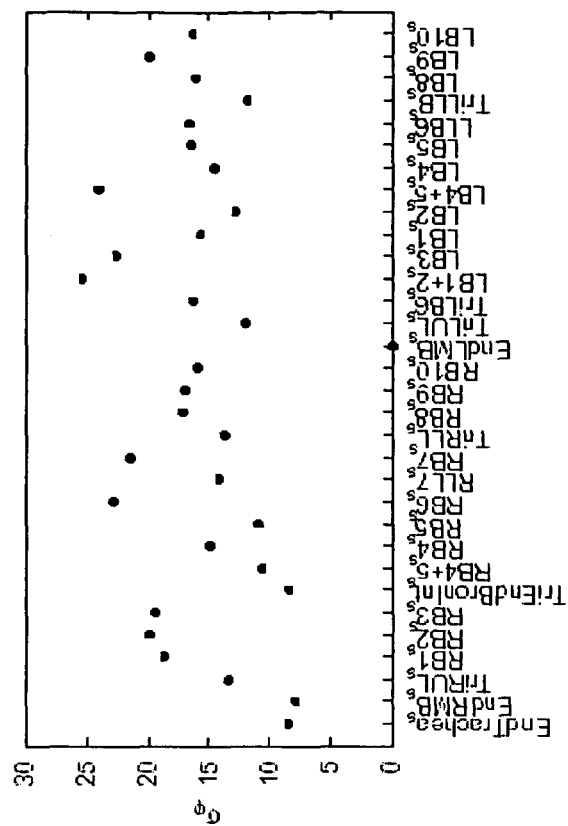
FIGS. 7A and 7B show variation of single segment measures in a population average.
Figure 7A:
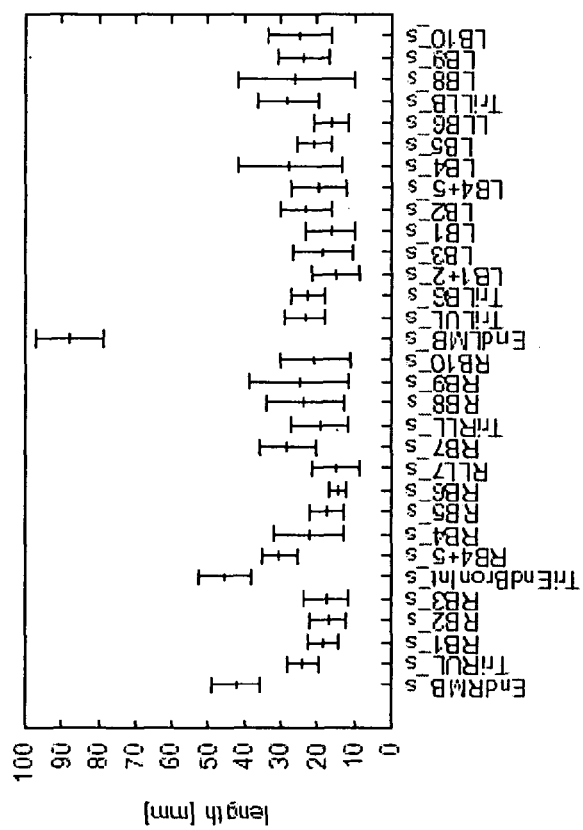

FIGS. 7A and 7B show the variation of the two single segment measures, taken from 17 trees. Both the length measure and the spatial orientation measure have a relatively small variation and provide reliable criteria for identifying segments.

For the inter-segment relationship the following parameters are recorded:

Inheritance relationship—for, e.g., every pair of anatomically named segments the inheritance relationship is recorded as a label from the set {PARENT, CHILD, SIBLING}.

Topological distance—for, e.g., every pair of anatomically named segments the minimum and maximum value of the topological distance is recorded.

Angle between segments—for, e.g., every pair $\vec{s}_n$ and $\vec{s}_m$ of anatomically named segments the average angle and its standard deviation are computed with $$\vec{\mu}_\varphi = \frac{1}{T} \sum_{i=0}^{T-1} \cos^{-1} \frac{\vec{S}_m \cdot \vec{S}_n}{|\vec{S}_m| \cdot |\vec{S}_n|} \quad (4.3)$$

and $$\sigma_\varphi = \sqrt{\frac{1}{T-1} \sum_{i=0}^{T-1} \left( \cos^{-1} \frac{\vec{S}_m \cdot \vec{S}_n}{|\vec{S}_m| \cdot |\vec{S}_n|} - \vec{\mu}_\varphi \right)^2} \quad (4.4)$$

respectively.

Spatial relationship between segments—for, e.g., every pair of $\vec{s}_n$ and $\vec{s}_m$ of anatomically named segments the average spatial relationship is computed with $$\vec{\mu}_{SR} = \frac{\sum_{i=0}^{T-1} \vec{S}_{m_c} - \vec{S}_{n_c}}{T} \quad (4.5)$$

and the unit vector of $\vec{\mu}_{SR}$ is recorded in the population average. The average variation of the spatial relationship is computed as $$\sigma_{SR} = \sqrt{\frac{1}{T-1} \sum_{i=0}^{T-1} \left( \cos^{-1} \frac{(\vec{S}_{m_c} - \vec{S}_{n_c}) \cdot \vec{\mu}_{SR}}{|\vec{S}_{m_c} - \vec{S}_{n_c}| \cdot |\vec{\mu}_{SR}|} \right)^2} \quad (4.6)$$

Figure 8A:
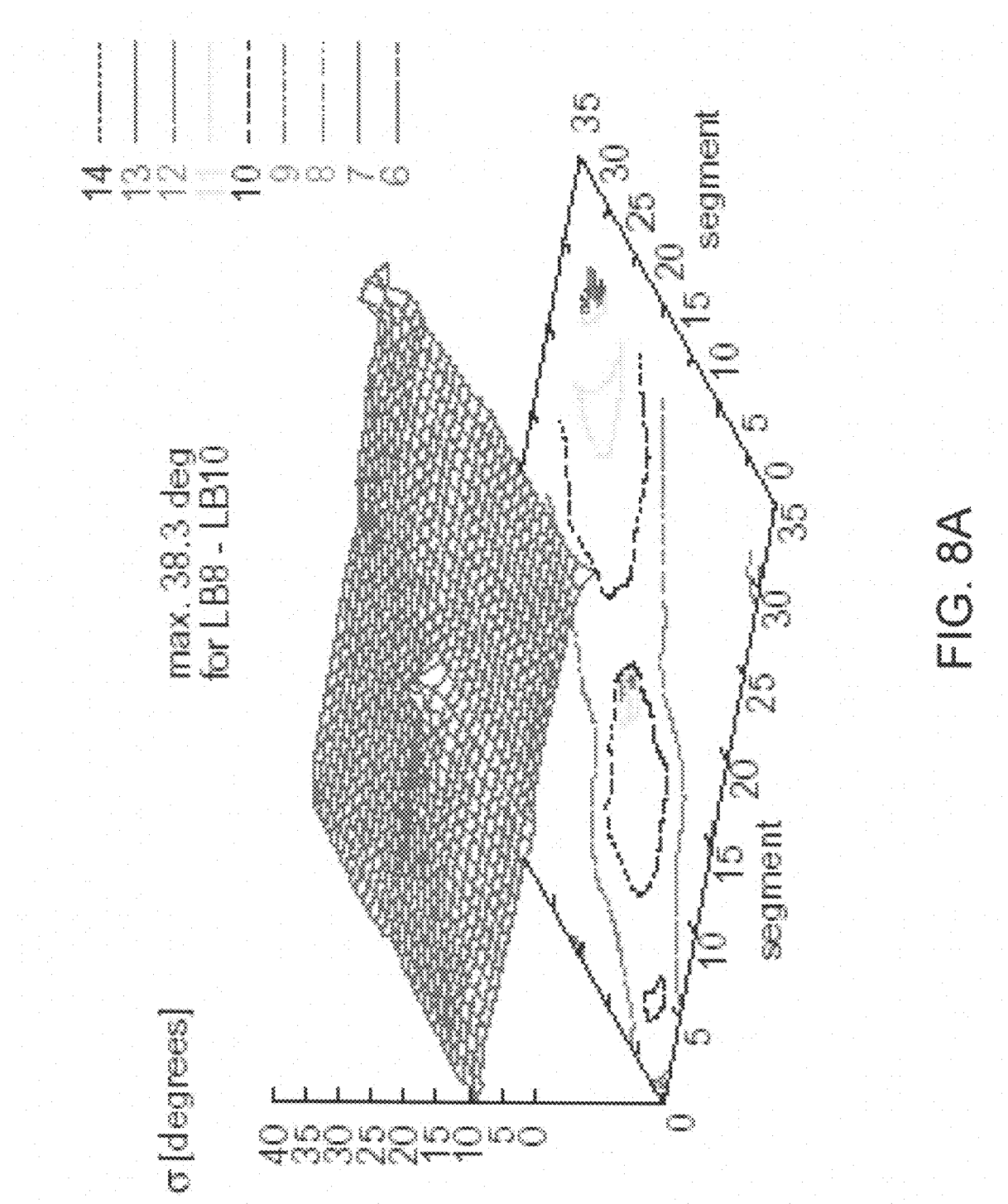
FIGS. 8A-8C show the variation of various inter-segment measures compiled from measurements made on 17 different trees.
Figure 8B:
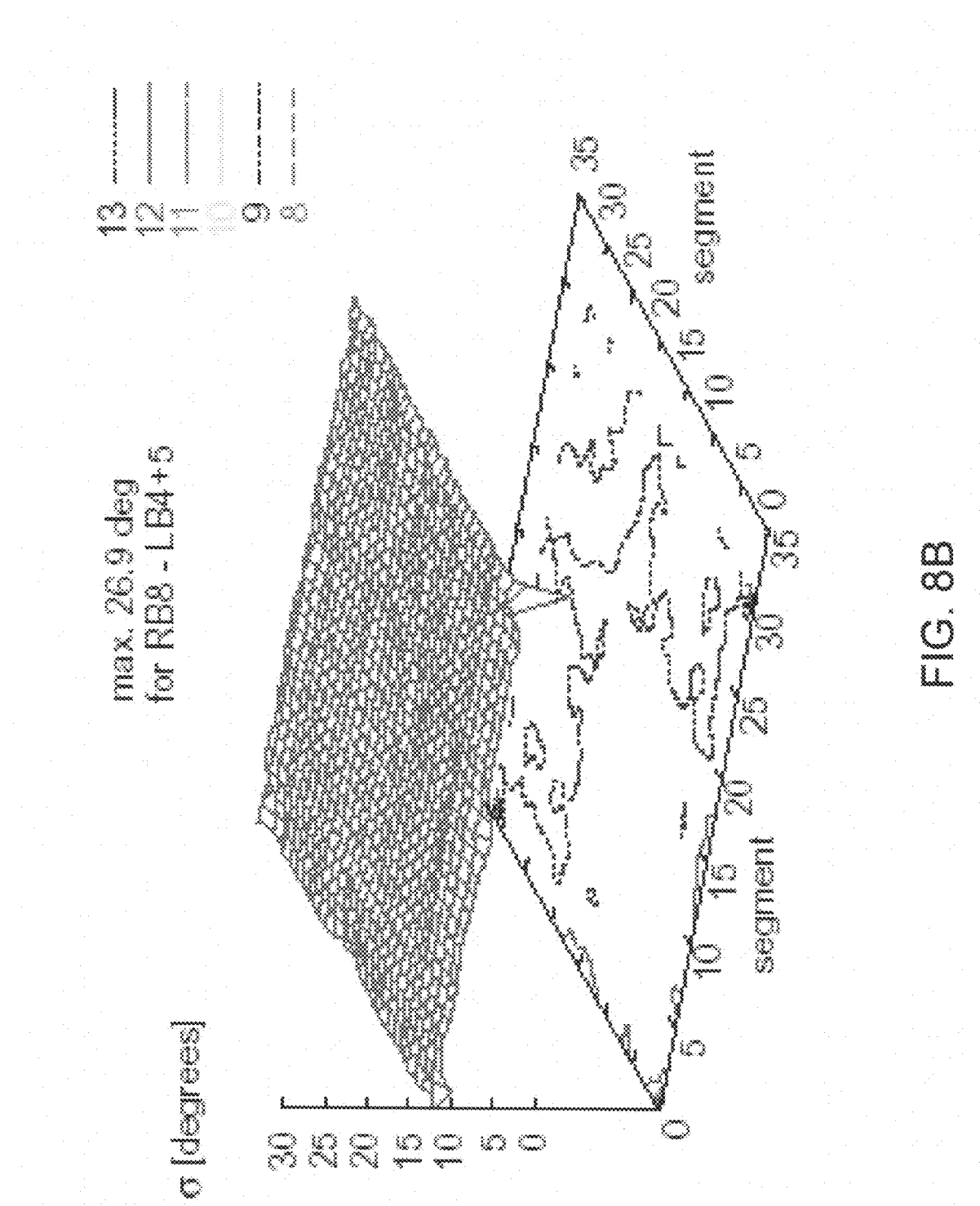
Figure 8C:
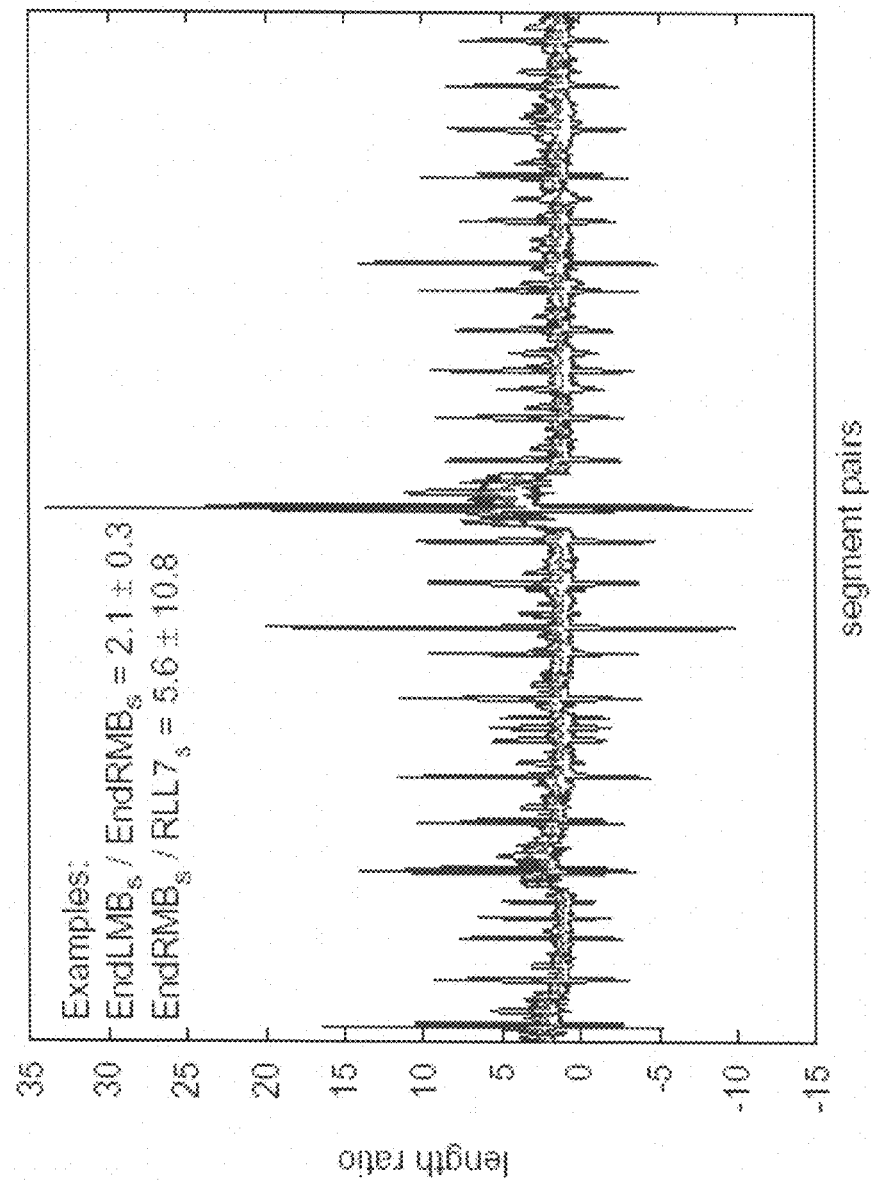

FIGS. 8A-8C show the variation of various intra-segment measures. One can see that the angle between segments and the spatial relationship between segments provide relatively good measures with only moderate variability. On the other hand, measuring the length ratio of segments does not provide a good measure, as can be seen in FIG. 8C. The variability for many pairs of segments is too big.

Introducing Parallel Edges

Figure 9:
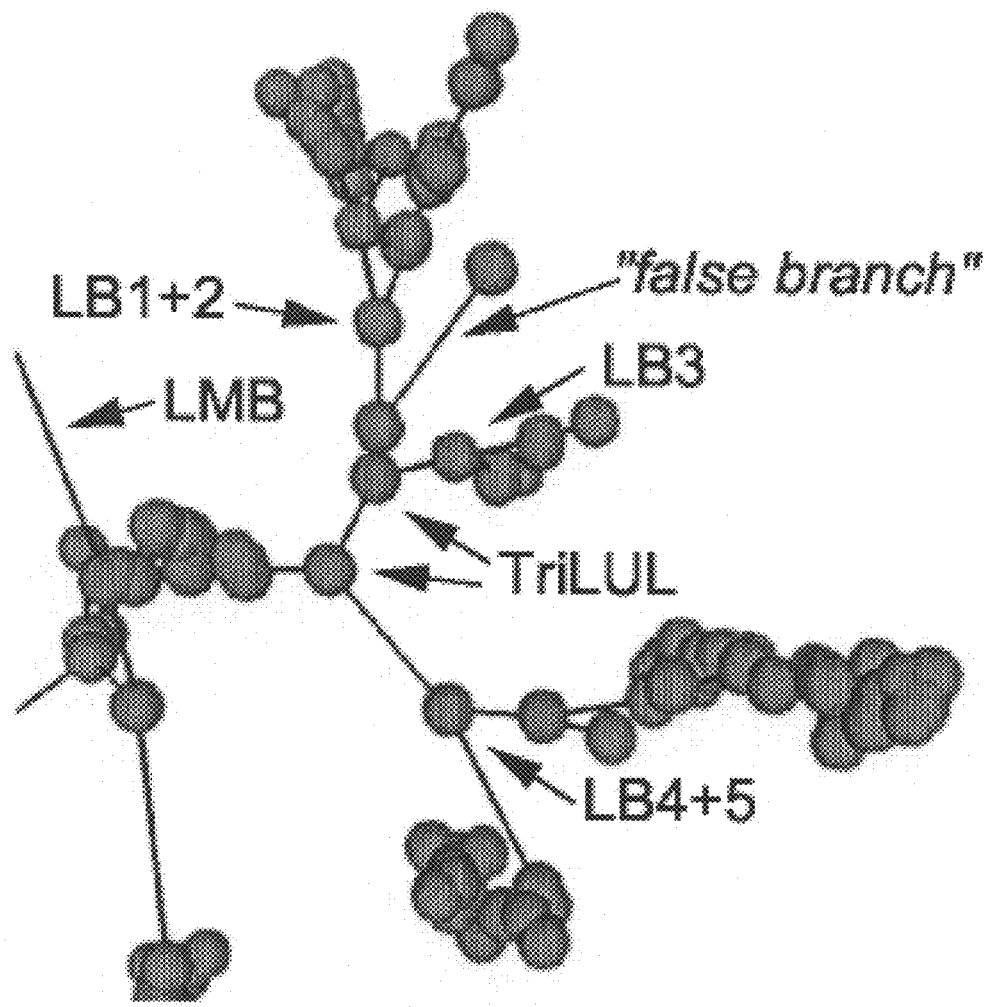
FIG. 9 illustrates an example of a long "false" branch.

In the embodiment of the intra-subject branch-point matching method described above, short branches (likely to be false) were pruned out from the target trees. While this is an appropriate and effective method of preprocessing trees for intra-subject matching, pruning only works in a limited way when preparing a tree for anatomical labeling. FIG. 9 illustrates the reason for that.

The problem is that sometimes airway trees contain relatively long "false" branches. Sometimes these branches are not actually false; they do really exist in the target tree. They represent anatomical segments that are not typical and are likely not represented in the population average. The "false" branch in FIG. 9 is such an example. Pruning with a fixed threshold cannot remove such branches without removing desired branches as well (e.g., TriLUL-LB3 in FIG. 9). For the intra-subject matching, the presence of such extra branches generally does not matter because they most likely exist in both trees. But for the labeling process presently described they do matter because they are not contained in the population average and consequently they cause a mismatch for the topological distances.

Figure 10:
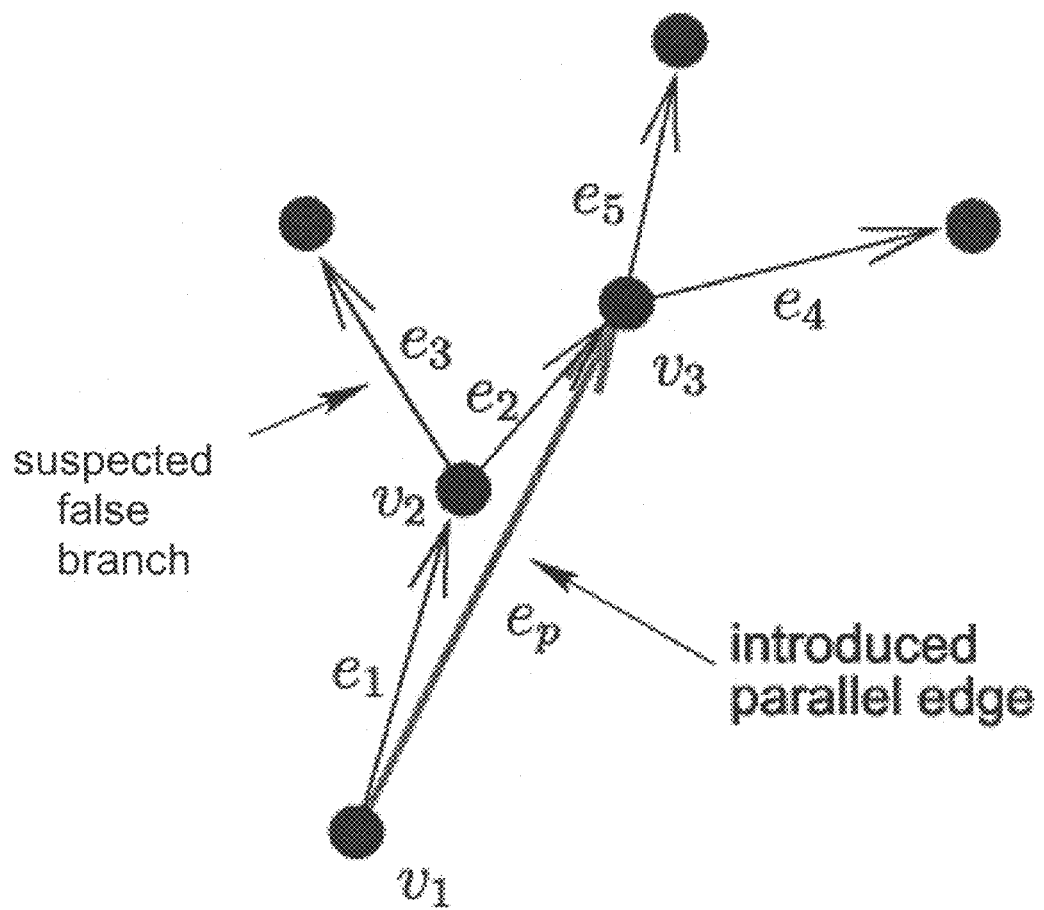
FIG. 10 illustrates one manner of addressing a suspected false branch through the introduction of a "parallel" edge. In this figure, edge $e_3$ might be a false branch. An edge $e_p$ parallel to edges $e_1$ and $e_2$ is added.

In some embodiments of the present labeling methods, a solution is to introduce "parallel" edges into the target tree prior to building the association graph. For example, parallel edges may be introduced for all edges that might be false in the anatomical textbook-sense. For example, in FIG. 10, a parallel edge $v_p$ is added to the tree if edge $e_1$ has two out-edges, among which one is a terminal edge ($e_3$). Additionally, the angle between $e_1$ and $e_2$ has to be close to 180 degrees. This second criterion my be judged by taking the ratio of distances between vertices $v_1$, $v_2$, and $v_3$. A parallel edge is added if $|v_3-v_1|/(|e_1|+|e_2|) \geqq 0.9$ and $|e_1|+|e_2|>5$ voxels or $|v_3-v_1|/(|e_1|+|e_2|) \geqq 0.7$ and $|e_1|+|e_2|>5$ voxels.

In one respect, the present methods and devices that involve the introduction of such edges may be characterized as an automated method comprising, or a computer readable medium comprising machine readable instructions for, respectively, accessing a representation of a target tree, the representation having edges and vertices; identifying a vertex in the representation that includes a first out-edge, a second out-edge, and an in-edge, where the second out-edge is a terminal edge and where a first vertex defines one end of the first out-edge and a second vertex defines one end of the in-edge; and introducing an edge to the representation that extends between the first vertex and the second vertex. In another respect, such methods and devices may also include, or further comprise machine readable instructions for, accessing data that includes (a) a reference tree having labels and reference tree edges, and (b) inheritance relationship data about some of the reference tree edges; and building a tree association graph, where the building includes: adding a first edge to the tree association graph if (i) a corresponding edge of the representation has an inheritance relationship that is the same as the inheritance relationship of a corresponding reference tree edge, and (ii) the topological distance between a vertex of the first edge and a vertex of the corresponding edge of the representation tree is within a certain limit.

After introducing the parallel edges the mutual inheritance relationship and topological distance for, e.g., every pair of vertices and every pair of edges may be 5 determined. First the vertex relationship array $R_v$ is computed using Algorithm 1 shown in FIG. 2. Based on $R_v$, which contains the inheritance relationship and the minimum and maximum topological distance between any two edges in the associated tree, the edge relationship array $R_e$ is computed with Algorithm 3 shown in Table 3:

TABLE 3

Algorithm 3

```
Input:  𝒯 : tree
        ℛᵥ: vertex relationship array
Output: ℛₑ : edge relationship array
re-size ℛᵥ, N, N)
for every element in ℛᵥ do
    r ← "N/A"
    d_min ← d_max ← 0
for every edge e₁t in 𝒯 do
    for every edge e₂t in 𝒯 do
        t₁ ← target Vertex (e₁)
        t₂ ← target Vertex (e₂)
        ℛₑ (e₁, e₂)·r ← ℛᵥ (t₁, t₂)·r
        ℛₑ (e₂, e₁)·r ← ℛᵥ (t₂, t₁)·r
        ℛₑ (e₁, e₂)·d_min ← ℛᵥ (t₁, t₂)·d_min
        ℛₑ (e₂, e₁)·d_min ← ℛᵥ (t₂, t₁)·d_min
        ℛₑ (e₁, e₂)·d_max ← ℛᵥ (t₁, t₂)·d_max
        ℛₑ (e₂, e₁)·d_max ← ℛᵥ (t₂, t₁)·d_max
        if ℛₑ(e₁, e₂)·r = "SIBLING" then
            ℛₑ (e₁, e₂)·d_min ← ℛₑ (e₁, e₂)·d_min - 1
            ℛₑ (e₂, e₁)·d_min ← ℛₑ (e₂, e₁)·d_min - 1
            ℛₑ (e₁, e₂)·d_max ← ℛₑ (e₁, e₂)·d_max - 1
            ℛₑ (e₂, e₁)·d_min ← ℛₑ (e₂, e₁)·d_max - 1
```

Note that the relationship of every pair of edges is computed in this example, including parallel edges, which have a CHILD-CHILD inheritance relationship.

Introducing parallel edges allows the embodiment of the present matching algorithms to chose from two possibilities—either use the original edges and ignore the parallel edge, or use the parallel edge and ignore the original edges. Two parallel edges cannot be used simultaneously in the labeled end-result. Again referring to FIG. 10, $e_1$ and $e_p$ have a SIBLING relationship. At the same time, $e_1$ is a parent of $e_4$ and $e_p$ is a parent of $e_4$ as well. To make a simultaneous labeling of $e_1$, $e_p$ and $e_4$ possible, all of the relationships

would have to be contained in the population average. But this constellation can only occur in the presence of parallel edges, and parallel edges are not allowed to be in the population average. Hence a simultaneous labeling of parallel edges is not possible.

Building Association Graph

In some embodiments of the present labeling methods, the first step comprises pruning the target-tree of short branches. A fixed threshold value of 5 mm may be used to make sure that no essential branches are pruned away, yet obviously false branches are removed. This reduces the problem size and shortens the overall computation time.

Next, parallel edges as described above may be added to the target-tree.

Vertices may be added to the association graph by pairing segments from the population average with potentially corresponding edges from the target tree. Edges may be added to the association graph if the corresponding edges in the target tree have the same inheritance relationship as the corresponding segments in the population average, and if the topological distance is within the limits given by the population average.

In some embodiments of the present labeling methods, every vertex and every edge in the association graph has a weight $W_{vertex}$=[0,1] and $w_{edge}$=[0,1], respectively, associated with it.

In some embodiments of the present labeling methods, every association graph vertex weight $W_{vertex}$ is based on the single-segment measures and is computed by $$\omega_{vertex} = \exp\left(-\frac{l-\mu_l}{2\sigma_l^2}\right) \cdot \exp\left(-\frac{\varphi_{SO}}{2\sigma_{SO}^2}\right) \quad (4.7)$$

with $$\varphi_{SO} = \cos^{-1}\frac{\vec{S}_n \cdot \vec{\mu}_{SO}}{|\vec{S}_n| \cdot |\vec{\mu}_{SO}|} \quad (4.8)$$

In some embodiments of the present labeling methods, every association graph edge weight $w_{edge}$ is based on the inter-segment measures and is computed by $$\omega_{edge} = \exp\left(-\frac{(\varphi_\phi - \mu_\varphi)^2}{2\sigma_\varphi^2}\right) \cdot \exp\left(-\frac{\varphi_{SR}^2}{2\sigma_{SR}^2}\right) \quad (4.9)$$

with $$\varphi_\phi = \cos^{-1}\frac{\vec{S}_n \cdot \vec{S}_m}{|\vec{S}_n| \cdot |\vec{S}_m|} \quad (4.10)$$

and $$\varphi_{SR} = \cos^{-1}\frac{\vec{S}_n \cdot \vec{\mu}_{SR}}{|\vec{S}_n| \cdot |\vec{\mu}_{SR}|} \quad (4.11)$$

In some embodiments of the present labeling methods, only vertices and edges with a value greater than 0.1 are added to the association graph. This helps limit the size of the association graph and consequently reduces the computing time when searching for the maximum clique.

Finding Maximum Weighted Clique

In some embodiments of the present labeling methods, the maximum clique in the association graph is found in a manner similar to the version of Algorithm 2 (Table 1 above). The only differences are that size is substituted with weights w that were assigned to the vertices and edges of the association graph, and lines 13 and 14 of Algorithm 2 are omitted because the remaining edges and vertices cannot be predicted and consequently an early termination is not possible. The clique with the biggest sum $\Omega = \Sigma_i^w{}_{vertexi} + \Sigma_j^w{}_{edgej}$ is sought.

One might use the average weight of all vertices and edges as measure for the total weight of a clique. However, this would have the disadvantage that single edges or vertices with below-average weight would not be included into the resulting maximum clique. Summing up the weights avoids this.

Reducing Computing Time

The problem of finding the maximum clique is NP-complete. Garey et al. (1979). One way of keeping the computing time down is to reduce the problem size. In the case of the tree-labeling, this may be done by a stepwise labeling.

Figures 11A, 11B, 11C:
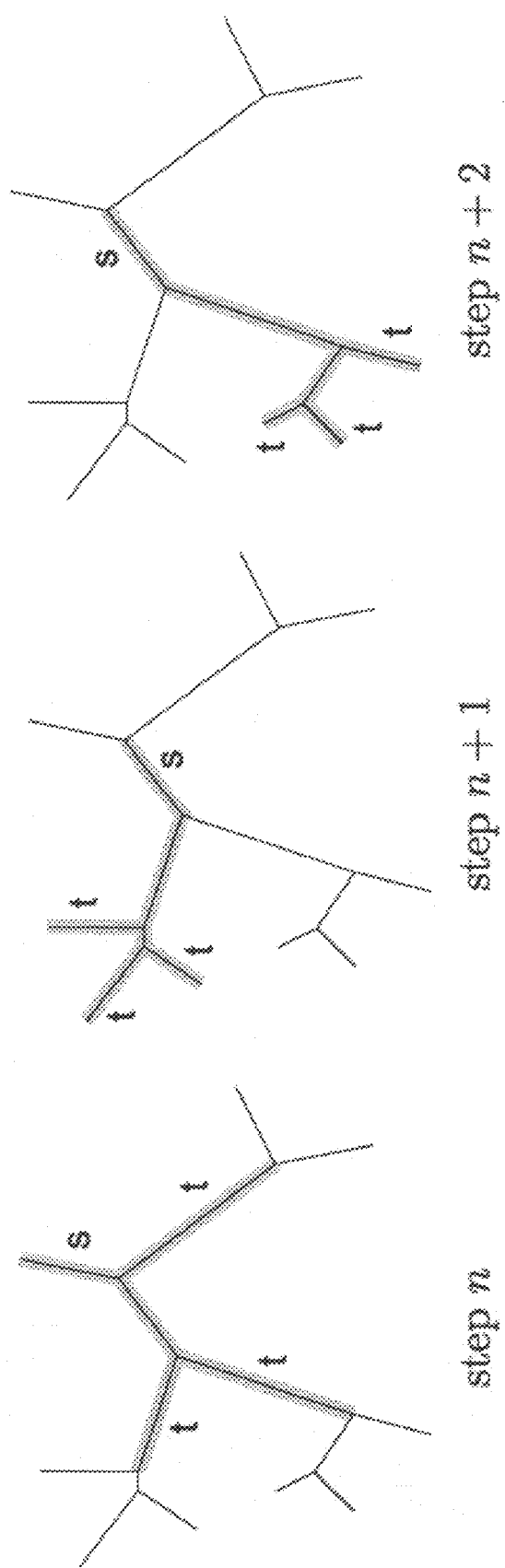
FIGS. 11A-11C illustrate a sequence of labeling steps designed to reduce computing time by splitting the task into sub-problems. Segments labeled during a step are gray. The labels 's' and 't' mark start- and terminal-segments, respectively.

In some embodiments of the present labeling methods, only a sub-tree is labeled during one labeling step. A sequence of labeling steps is illustrated in FIGS. 11A-11C. Every labeling step starts from a segment that already has its final label assigned to it (marked with a 's' in FIGS. 11A-11C). Terminal segments (marked with a 't' in FIGS. 11A-11C) are used as guides only and do not receive their final label at this point. The segments in-between the start segment and the terminal segments receive their final labels.

Applying this stepwise labeling results in a significant speedup of the labeling process. A complete tree is labeled in a few seconds, whereas an attempt of labeling an entire tree in one single step can take several hours. At the same time, the accuracy of the assigned labels is preserved.

Use Lobe-Information to Increase Quality of Labeling Result

Information about the location of lung lobes can be used to restrict the search space when assigning anatomical labels.

The human lung consists of five distinct lung lobes. Anatomical pre-knowledge provides information about which anatomical airway labels are contained in which lung lobe.

In some embodiments of the present labeling methods, given an accurate lobe segmentation, the process of assigning anatomical labels can be subdivided into five separate tasks. Each lobe is treated as a separate entity and only airways within a lobe, together with the sub-set of anatomical labels that are known to belong to that lobe, are considered at a time. This results in a restriction of the search space because the possible targets where a label may be assigned to are reduced. This should not only speeds up the labeling process, but more importantly it should guarantee that every airway segment label is assigned within its correct lobe. As a result, the risk of mislabeling a segment should be significantly reduced and the overall quality of the labeling result should increase.

Use of lobe information as just described is not implemented in the embodiment (e.g., the software) of the present labeling methods described in Appendix 1 of U.S. Provisional Patent Application Ser. No. 60/568,184.

Implementation

In some embodiments of the present labeling methods, the graph-related parts may be realized with the help of the Boost Graph Library, Siek et al. (2002). The complete labeling algorithm may be implemented as a command-line application written in ANSI C++ (e.g., one example of machine-readable instructions). Such a program can take one XML tree file as input and can write the labels back into the same file. A description of relevant XML files appears above. Labeling a full-sized in-vivo tree containing 200-300 vertices requires a computing time of about 5 seconds, measured on a single AMD Athlon™ CPU running at a clock rate of 1.2 GHz.

In some embodiments of the present labeling methods, a separate command-line application computes the population average. A text file defines the trees (contained in XML tree files) that can be used for the definition of the population average. The results are saved into an ASCII file (about 80 kBytes in size) and will be loaded by the labeling program during initialization. The ASCII format allows platform independent usage of the population average while being one of the most straightforward formats to define and implement. Computing the population average may take up to a half a minute per input tree (depending on the tree size), but may be done only once.

Results

Figure 12:
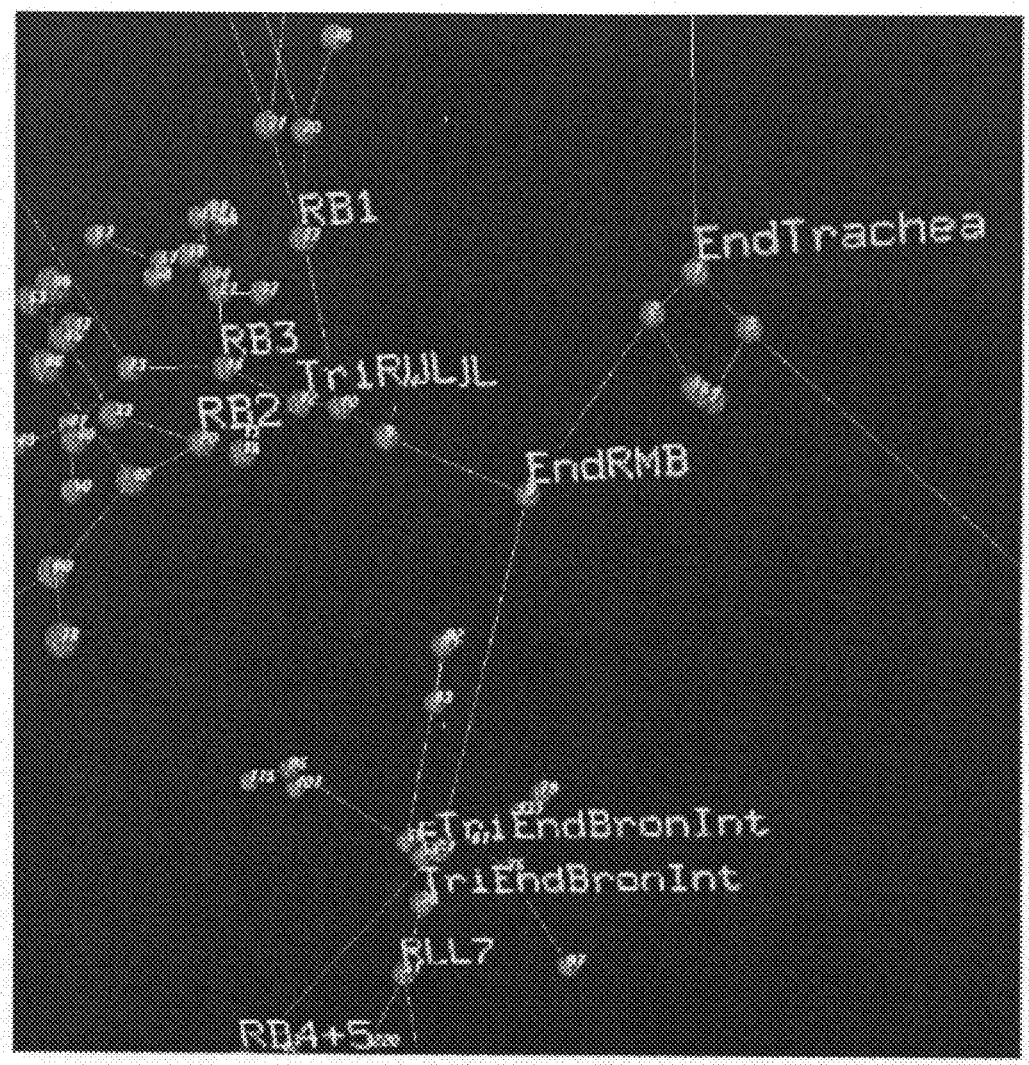
FIG. 12 shows an example of the results of branch-point labeling using one embodiment of the present labeling methods.

FIG. 12 shows a detail view of a typical result of automated anatomical labeling of an in-vivo tree according to one embodiment of the present labeling methods. Note that correct labels are assigned despite the presence of false branches.

Validation of the embodiment of our branch-point labeling program presented here (minus the use of lobe-information described above) was performed with in-vivo data sets. The accuracy of the program was evaluated by comparing the automated results against an independent standard provided by a human expert.

Independent Standard

Scans from a total of 17 subjects, 10 healthy and 7 diseased, were available. For each subject, a total lung capacity scan (TLC, 85% lung-volume) was taken as the basis for generating the independent standard. In each volume the airway-tree was segmented and skeletonized by automated methods, and the graph representation of the airway-trees was then available to the labeling and matching processes.

An application was written that allowed human experts to perform the tree-labeling by hand. Using this tool, all 17 TLC trees were hand-labeled by a human expert. These hand-labeled trees were then used as gold-standard for the validation of the automated method.

Automated Method

The leave-one-out jackknife) method was used for building the population average and for testing the automated labeling. All trees but one were used for building the population average, and the automated program (the program may, as a whole, also be characterized as an algorithm) was then run on the one tree left out. This procedure was repeated for all 17 TLC trees.

Tables 4 and 5 list the validation results for the labeling algorithm. In the first case (Table 4) the segment labels were verified for accuracy. In the second case (Table 5) the branch-point labels were validated.

TABLE 4

| Subject | Correct label | Incorrect label | Computer label not found in the reference set | Reference label not found among computer labels |
| --- | --- | --- | --- | --- |
| Normal 1 (brp001tlc) | 31 | 1 | 0 | 6 |
| Normal 2 (brp002tlc) | 28 | 0 | 4 | 7 |
| Normal 3 (brp003tlc) | 32 | 0 | 0 | 7 |
| Normal 4 (brp004tlc) | 29 | 0 | 2 | 10 |
| Normal 5 (brp005tlc) | 18 | 2 | 7 | 11 |
| Normal 6 (brp006tlc) | 28 | 0 | 5 | 5 |
| Normal 7 (brp007tlc) | 30 | 1 | 1 | 10 |
| Normal 8 (brp008tlc) | 32 | 0 | 0 | 9 |
| Normal 9 (brp009tlc) | 25 | 1 | 7 | 4 |
| Normal 10 (brp010tlc) | 22 | 2 | 8 | 8 |
| Diseased 1 (h005tlc) | 23 | 2 | 2 | 6 |
| Diseased 2 (h006tlc) | 27 | 1 | 1 | 7 |
| Diseased 3 (h008tlc) | 27 | 0 | 0 | 10 |
| Diseased 4 (h009tlc) | 33 | 0 | 0 | 5 |
| Diseased 5 (h012tlc) | 24 | 2 | 1 | 10 |
| Diseased 6 (h014tlc) | 24 | 2 | 4 | 9 |
| Diseased 7 (h016tlc) | 28 | 0 | 2 | 7 |
| Total | 461 (97.1%) | 14 (2.9%) | | |

TABLE 5

| Subject | Correct label | Incorrect label | Computer label not found in the reference set | Reference label not found among computer labels |
| --- | --- | --- | --- | --- |
| Normal1 (brp001tlc) | 29 | 3 | 0 | 6 |
| Normal2 (brp002tlc) | 27 | 1 | 4 | 7 |
| Normal3 (brp003tlc) | 29 | 3 | 0 | 7 |
| Normal4 (brp004tlc) | 26 | 3 | 2 | 10 |

TABLE 5-continued

| Subject | Correct label | Incorrect label | Computer label not found in the reference set | Reference label not found among computer labels |
|---|---|---|---|---|
| Normal5 (brp005tlc) | 15 | 5 | 7 | 11 |
| Normal6 (brp006tlc) | 22 | 6 | 5 | 5 |
| Normal7 (brp007tlc) | 24 | 7 | 1 | 10 |
| Normal8 (brp008tlc) | 29 | 3 | 0 | 9 |
| Normal9 (brp009tlc) | 24 | 2 | 7 | 4 |
| Normal10 (brp010tlc) | 21 | 3 | 8 | 8 |
| Diseased (h005tlc) | 18 | 7 | 2 | 6 |
| Diseased (h006tlc) | 24 | 4 | 1 | 7 |
| Diseased (h008tlc) | 23 | 4 | 0 | 10 |
| Diseased (h009tlc) | 28 | 5 | 0 | 5 |
| Diseased (h012tlc) | 21 | 5 | 1 | 10 |
| Diseased (h014tlc) | 19 | 7 | 4 | 9 |
| Diseased (h016tlc) | 25 | 3 | 2 | 7 |
| Total | 404 (85.1%) | 71 (14.9%) | | |

Figure 13:
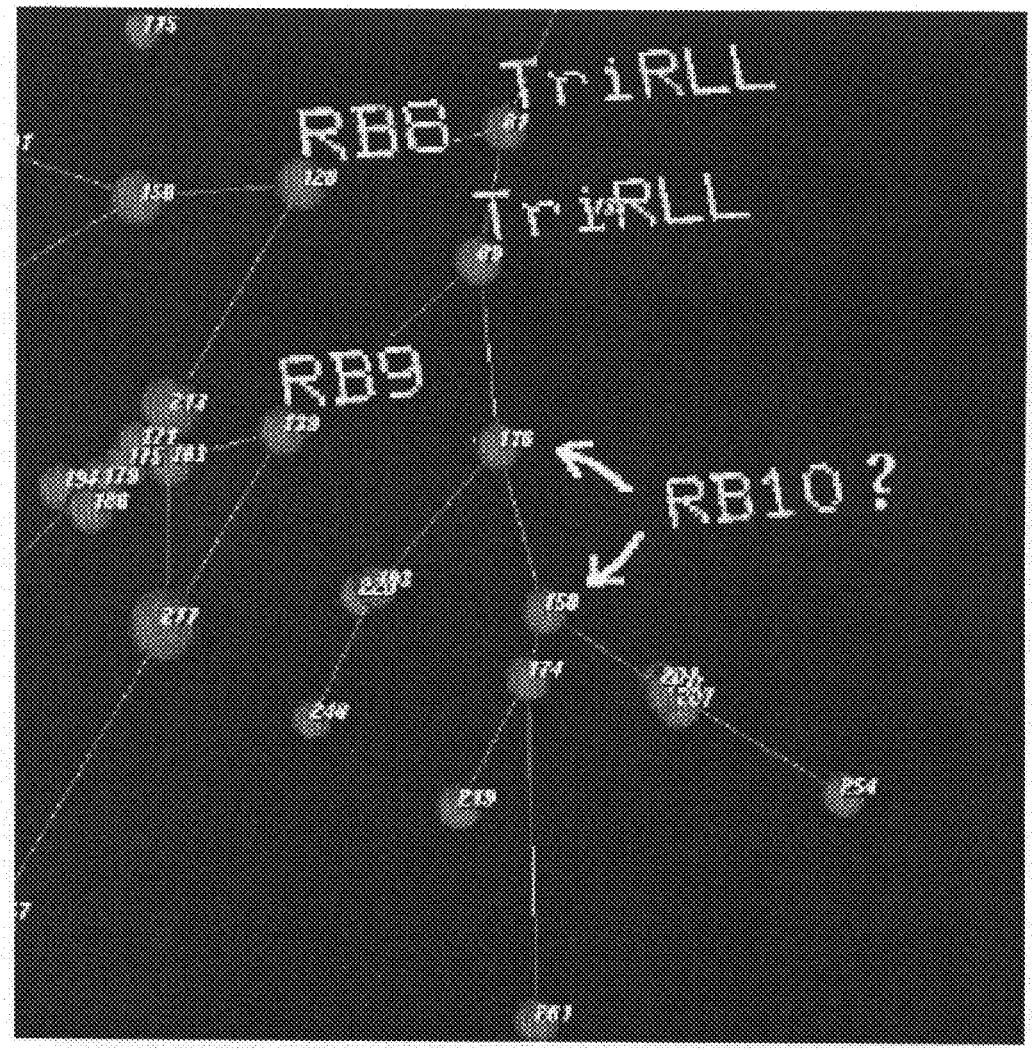
FIG. 13 illustrates an example of a terminal-label problem. It is not entirely in this figure which of the two branch-points is the true end-point of the RB10 segment.

85.1% of the assigned labels are correct. The number of correctly assigned segment labels is higher because it is difficult for the automated algorithm to label terminal 15 branch-points. A terminal branch-point is the highest-generation branch-point with anatomical label within a branch. Because no more labels are to be found beyond a terminal branch-point, the labeling algorithm does not have guide segments when assigning the label. This makes it difficult to find the exact branch-point. FIG. 13 illustrates this issue.

It was surprising and unexpected that the automated labeling identified a number of human errors. After reviewing the cases of disagreement between the independent standard and the automated result, we were able to identify 5 cases where a label was misplaced by the human expert.

While the embodiments of the present labeling methods (and devices) have been discussed in the context of the human airway tree, those of ordinary skill in the art will understand that they are also applicable to labeling aspects of any other artificial or natural tree structure for which a naming convention exists or is desired.

The present methods and devices are not intended to be limited to the particular forms disclosed. Rather, they are to cover all modifications, equivalents, and alternatives falling within the scope of the claims. The appended claims are not to be interpreted as including means-plus-function limitations, unless such a limitation is explicitly recited in a given claim using the phrase(s) "means for" and/or "step for," respectively.

REFERENCES

Each of the following references is specifically incorporated by reference in each location it is cited above:

Ballard and Brown, In: *Computer Vision. Prentice Hall PTR*, 1982.
Boyden, In: *Segmental anatomy of the lungs*, McGraw-Hill, 1955.
Carraghan and Pardalos, *Operations Research Letters*, 9:375-382, 11 1990.
Foley, *Computer Graphics: Principles and Practice*, Addison-Wesley, 1990.
Garey and Johnson, In *Computers and intractability, a guide to the theory of NP-completeness*, W. H. Freeman and Company, 1979.
Kitaoka et al., In: *Automated Nomenclature Labeling of the Bronchial Tree in 3D-CT Lung Images*, Tokyo, Japan, 1-11, 2002.
Mori et al., *IEEE Transactions on Medical Imaging*, 19:103-114, 2000.
Ostergard, *Discrete Applied Mathematics*, 195-205, 2002
Palágyi et al., In: *Proc. 18th Int. Conf. Information Processing in Medical Imaging*, IPMI2003, Ambleside, UK, Springer, 222-233, 2003.
Pardalos et al., In: *High Performance Algorithms and Software in Nonlinear Optimization*, HPSNO97 conference Ischia, Italy, June, 297-300, 1999.
Park, In: *Registration of linear structures in 3-D medical images*, Osaka Univers., Japan, Dept. of Informatics and Mathematical Science, 2002.
Pelillo et al., *IEEE Transactions on Pattern Analysis and Machine Intelligence*, 21:1105-1120,1999.
Pisupati et al., In: *Mathematical Methods in Biomedical Image Analysis*, Proc. of the Workshop, 160-169, 1996a.
Pisupati et al., In: *Geometric Tree Matching with applications to 3D Lung Structures*, Proc. of the $12^{th}$ Annual Symposium on Computational Geometry, Philadelphia, Pa., 419-20, 1996b.
Siek et al., In: *The Boost Graph Library*, Addison-Wesley, 2002.
Tschirren et al., In: *Branchpoint Labeling and Matching in Human Airway Trees*, SPIE Medical Imaging, San Diego, Calif., 2003.
Tschirren et al., In: *Radiological Society of North America*, RSNA, 88th Scientific Assembly and Annual Meeting, Chicago, Ill., 2002a.
Tschirren et al., In: *Segmentation, Skeletonization, and Branchpoint Matching—A Fully Automated Quantitative Evaluation of Human Intrathoracic Airway Trees*, MICCAI, Tokyo, Japan, 2002b.

We claim:

1. A non-transitory computer readable medium comprising machine readable instructions for:
   accessing a first representation of an airway tree of a human subject;
   accessing a second representation of the airway tree of the human subject;
   automatically pruning at least a portion of the first representation, including:
      deleting from the first representation of the airway tree a terminal branch having a length shorter than a pre-defined threshold length;
      deleting from the first representation of the airway tree a vertex having an in-edge and only one out-edge; and replacing the in-edge and out-edge of the deleted vertex with a single edge.

2. The computer readable medium of claim 1, further comprising machine readable instructions for:
   automatically pruning at least a portion of the second representation.

3. The computer readable medium of claim 2, the first and second representations of the airway tree each including vertices and one or more terminal branches, and the automatically pruning at least a portion of the first representation including:
   deleting from the first representation of the airway tree any terminal branch having a length shorter than a pre-defined threshold length.

4. The computer readable medium of claim 3, where the automatically pruning at least a portion of the second representation includes:
deleting from the second representation of the airway tree any terminal branch having a length shorter than a predefined threshold length.

5. The computer readable medium of claim 4, where the automatically pruning at least a portion of the first representation includes:
deleting from the first representation of the airway tree any vertex having an in-edge and only one out-edge; and
replacing the in-edge and out-edge of each deleted vertex from the first representation with a single edge.

6. The computer readable medium of claim 5, where the automatically pruning at least a portion of the second representation includes:
deleting from the second representation of the airway tree any vertex having an in-edge and only one out-edge; and
replacing the in-edge and out-edge of each deleted vertex from the second representation with a single edge.

7. The computer readable medium of claim 1, the first and second representations of the airway tree each including a carina and two main bronchi, each main bronchi including an end point, the computer readable medium further comprising machine readable instructions for:
identifying the carina and the end points of the two main bronchi in the first and second representations of the airway tree.

8. The computer readable medium of claim 7, further comprising machine readable instructions for:
matching the identified carina and end points of the two main bronchi from the first representation with the identified carina and end points of the two main bronchi from the second representation.

9. The computer readable medium of claim 8, further comprising machine readable instructions for:
identifying some remaining major branch-points in the first and second representations of the airway tree, the remaining major branch-points comprising branch-points that correspond to an entry point of either a lobe or a sub-lobe.

10. The computer readable medium of claim 9, further comprising machine readable instructions for:
matching the identified remaining major branch-points from the first representation with the identified remaining major branch-points from the second representation.

11. The computer readable medium of claim 10, further comprising machine readable instructions for:
matching a sub-tree from the first representation with a sub-tree from the second representation, where the sub-tree from a given representation is below the identified remaining major branch-points from the given representation.

12. The computer readable medium of claim 11, where each sub-tree includes a root point, and prior to matching the sub-tree from the first representation with the sub-tree from the second representation, one of the two sub-trees is translated such that the root points of the two sub-trees are superimposed.

13. The computer readable medium of claim 1, further comprising machine readable instructions for:
building a tree association graph.

14. The computer readable medium of claim 13, where the tree association graph has a maximum clique, and the computer readable medium also comprises machine readable instructions for:
identifying the maximum clique.

15. The computer readable medium of claim 13, where the tree association graph includes vertices, and the computer readable medium also comprises machine readable instructions for:
assigning the vertices to the tree association graph such that no inheritance relationships other than parent, child, or sibling exist among the vertices.

16. The computer readable medium of claim 1, where the first representation of the airway tree is based on a volumetric scan of the human subject taken using computed tomography.

17. The computer readable medium of claim 1, where the first representation of the airway tree is based on a volumetric scan of the human subject taken using magnetic resonance.

18. The computer readable medium of claim 1, where the airway tree is diseased.

19. A non-transitory computer readable medium comprising machine readable instructions for:
accessing a first representation of an airway tree of a human subject, the first representation including vertices;
accessing a second representation of the airway tree of the human subject, the second representation including vertices;
building a tree association graph, where the building includes determining whether two possible vertices of the tree association graph have a topological distance that falls within a range of acceptable topological distances; and
automatically pruning at least a portion of the first representation, including:
deleting from the first representation of the airway tree a vertex having an in-edge and only one out-edge; and
replacing the in-edge and out-edge of the deleted vertex with a single edge.

20. A non-transitory computer readable medium comprising machine readable instructions for:
accessing a first representation of an airway tree of a human subject, the first representation including vertices;
accessing a second representation of the airway tree of the human subject, the second representation including vertices; and
building a tree association graph, where the building includes assigning vertices to the tree association graph such that no inheritance relationships other than parent, child, or sibling exist among the vertices.

21. A non-transitory computer readable medium comprising machine readable instructions for:
accessing a first representation, the first representation including a segmented, skeletonized representation of an airway tree at a first lung volume of a human subject;
accessing a second representation, the second representation including a segmented, skeletonized representation of the airway tree at a second lung volume of a human subject; and
automatically pruning at least a portion of the first representation, including:
deleting from the first representation a vertex having an in-edge and only one out-edge; and
replacing the in-edge and out-edge of the deleted vertex with a single edge.

22. The computer readable medium of claim 21, further comprising machine readable instructions for:
automatically pruning at least a portion of the second representation.

23. The computer readable medium of claim 22, the first and second representations of the airway tree each including vertices and one or more terminal branches, and the automatically pruning at least a portion of the first representation including:
  deleting from the first representation of the airway tree any terminal branch having a length shorter than a pre-defined threshold length.

24. The computer readable medium of claim 23, where the automatically pruning at least a portion of the second representation includes:
  deleting from the second representation of the airway tree any terminal branch having a length shorter than a pre-defined threshold length.

25. The computer readable medium of claim 24, where the automatically pruning at least a portion of the first representation includes:
  deleting from the first representation of the airway tree any vertex having an in-edge and only one out-edge; and
  replacing the in-edge and out-edge of each deleted vertex from the first representation with a single edge.

26. The computer readable medium of claim 25, where the automatically pruning at least a portion of the second representation includes:
  deleting from the second representation of the airway tree any vertex having an in-edge and only one out-edge; and
  replacing the in-edge and out-edge of each deleted vertex from the second representation with a single edge.

27. The computer readable medium of claim 21, the first and second representations of the airway tree each including a carina and two main bronchi, each main bronchi including an end point, the computer readable medium further comprising machine readable instructions for:
  identifying the carina and the end points of the two main bronchi in the first and second representations of the airway tree.

28. The computer readable medium of claim 27, further comprising machine readable instructions for:
  matching the identified carina and end points of the two main bronchi from the first representation with the identified carina and end points of the two main bronchi from the second representation.

29. The computer readable medium of claim 28, further comprising machine readable instructions for:
  identifying some remaining major branch-points in the first and second representations of the airway tree, the remaining major branch-points comprising branch-points that correspond to an entry point of either a lobe or a sub-lobe.

30. The computer readable medium of claim 29, further comprising machine readable instructions for:
  matching the identified remaining major branch-points from the first representation with the identified remaining major branch-points from the second representation.

31. The computer readable medium of claim 30, further comprising machine readable instructions for:
  matching a sub-tree from the first representation with a sub-tree from the second representation, where the sub-tree from a given representation is below the identified remaining major branch-points from the given representation.

32. The computer readable medium of claim 31, where each sub-tree includes a root point, and prior to matching the sub-tree from the first representation with the sub-tree from the second representation, one of the two sub-trees is translated such that the root points of the two sub-trees are superimposed.

33. The computer readable medium of claim 21, further comprising machine readable instructions for:
  building a tree association graph.

34. The computer readable medium of claim 33, where the tree association graph has a maximum clique, and the computer readable medium also comprises machine readable instructions for:
  identifying the maximum clique.

35. The computer readable medium of claim 33, where the tree association graph includes vertices, and the computer readable medium also comprises machine readable instructions for:
  assigning the vertices to the tree association graph such that no inheritance relationships other than parent, child, or sibling exist among the vertices.

36. The computer readable medium of claim 21, where the first representation of the airway tree is based on a volumetric scan of the human subject taken using computed tomography.

37. The computer readable medium of claim 21, where the first representation of the airway tree is based on a volumetric scan of the human subject taken using magnetic resonance.

38. The computer readable medium of claim 21, where the airway tree is diseased.

* * * * *

UNITED STATES PATENT AND TRADEMARK OFFICE
CERTIFICATE OF CORRECTION

| | | |
|---|---|---|
| PATENT NO. | : 8,155,403 B2 | Page 1 of 1 |
| APPLICATION NO. | : 11/122974 | |
| DATED | : April 10, 2012 | |
| INVENTOR(S) | : Juerg Tschirren et al. | |

It is certified that error appears in the above-identified patent and that said Letters Patent is hereby corrected as shown below:

In the Specification

In column 1, lines 15-16, delete paragraph and insert
--This invention was made with government support under Grant No. HL-064368 awarded by the National Institutes of Health. The Government has certain rights in the invention.-- therefor.

Signed and Sealed this
Tenth Day of December, 2013

Margaret A. Focarino
*Commissioner for Patents of the United States Patent and Trademark Office*